United States Patent
Seifert

(10) Patent No.: US 8,868,208 B2
(45) Date of Patent: Oct. 21, 2014

(54) MR-COMPATIBLE IMPLANTABLE MEDICAL LEAD

(71) Applicant: Medtronic, Inc., Minneapolis, MN (US)

(72) Inventor: Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/755,358

(22) Filed: Jan. 31, 2013

(65) Prior Publication Data

US 2014/0114380 A1   Apr. 24, 2014

Related U.S. Application Data

(60) Provisional application No. 61/717,462, filed on Oct. 23, 2012, provisional application No. 61/723,012, filed on Nov. 6, 2012.

(51) Int. Cl.
| | |
|---|---|
| *A61N 1/00* | (2006.01) |
| *A61N 1/05* | (2006.01) |
| *A61N 1/362* | (2006.01) |
| *A61N 1/08* | (2006.01) |
| *A61N 1/39* | (2006.01) |

(52) U.S. Cl.
CPC . *A61N 1/08* (2013.01); *A61N 1/362* (2013.01); *A61N 1/0563* (2013.01); *A61N 2001/086* (2013.01); *A61N 1/3962* (2013.01)
USPC ........................................................ 607/116

(58) Field of Classification Search
USPC ........................................................ 607/116
See application file for complete search history.

(56) References Cited

U.S. PATENT DOCUMENTS

| | | |
|---|---|---|
| 5,676,694 A | 10/1997 | Boser et al. |
| 6,018,683 A | 1/2000 | Verness et al. |
| 6,871,091 B2 | 3/2005 | Wilkinson et al. |
| 6,944,489 B2 | 9/2005 | Zeijlemaker et al. |
| 6,985,775 B2 | 1/2006 | Reinke et al. |
| 7,050,855 B2 | 5/2006 | Zeijlemaker et al. |

(Continued)

FOREIGN PATENT DOCUMENTS

WO    2005053555 A1    6/2005

OTHER PUBLICATIONS (PCT/US2013/063336) PCT Notification of Transmittal of the International Search Report and the Written Opinion of the International Searching Authority, Mailed Dec. 20, 2013, 7 pages.

*Primary Examiner* — George Manuel
(74) *Attorney, Agent, or Firm* — Michael J. Ostrom; Stephen W. Bauer

(57) ABSTRACT

A medical electrical lead may include a lead body having a proximal end and a distal end, a conductive electrode shaft located near the distal end within the lead body, a coiled conductor extending within the lead body from the proximal end and coupled to a first end of the conductive electrode shaft, and an electrode located near the distal end of the lead body and coupled to an opposite end of the conductive electrode shaft as the coiled conductor. The lead may also include an energy dissipating structure located near the distal end of the lead body and formed from a conductive material that defines a lumen through which a portion of the coiled conductor extends. The portion of the coiled conductor extending through the lumen defined by the energy dissipating structure is formed to provide an interference contact with the energy dissipating structure.

22 Claims, 15 Drawing Sheets

(56) References Cited

U.S. PATENT DOCUMENTS

| | | |
|---|---|---|
| 7,174,219 B2 | 2/2007 | Wahlstrand et al. |
| 7,689,288 B2 | 3/2010 | Stevenson et al. |
| 7,751,903 B2 | 7/2010 | Stevenson et al. |
| 7,853,332 B2 | 12/2010 | Olsen et al. |
| 7,865,247 B2 | 1/2011 | Smith, Jr. et al. |
| 7,962,224 B1 | 6/2011 | Blischak |
| 7,966,075 B2 | 6/2011 | Johnson et al. |
| 8,000,801 B2 | 8/2011 | Stevenson et al. |
| 8,027,736 B2 | 9/2011 | Wahlstrand et al. |
| 8,160,717 B2 | 4/2012 | Ameri |
| 8,412,351 B2 | 4/2013 | Zeijlemaker et al. |
| 2005/0070972 A1 | 3/2005 | Wahlstrand et al. |
| 2005/0222647 A1 | 10/2005 | Wahlstrand et al. |
| 2006/0247747 A1 | 11/2006 | Olsen et al. |
| 2006/0247748 A1 | 11/2006 | Wahlstrand et al. |
| 2007/0185556 A1 | 8/2007 | Williams et al. |
| 2007/0208383 A1 | 9/2007 | Williams |
| 2007/0299490 A1 | 12/2007 | Yang et al. |
| 2008/0009905 A1 | 1/2008 | Zeijlemaker |
| 2008/0147154 A1 | 6/2008 | Gray et al. |
| 2008/0154346 A1 | 6/2008 | Smith et al. |
| 2008/0183230 A1 | 7/2008 | Kemmetmueller et al. |
| 2010/0016936 A1 | 1/2010 | Stevenson et al. |
| 2010/0023000 A1 | 1/2010 | Stevenson et al. |
| 2010/0042190 A1 | 2/2010 | Arnholt et al. |
| 2010/0160997 A1 | 6/2010 | Johnson et al. |
| 2010/0174349 A1 | 7/2010 | Stevenson et al. |
| 2010/0217262 A1 | 8/2010 | Stevenson et al. |
| 2010/0312294 A1 | 12/2010 | Martinez et al. |
| 2010/0318160 A1 | 12/2010 | Stevenson et al. |
| 2011/0034979 A1 | 2/2011 | Min et al. |
| 2011/0040343 A1 | 2/2011 | Johnson et al. |
| 2011/0054293 A1 | 3/2011 | Markowitz et al. |
| 2011/0066212 A1* | 3/2011 | Stevenson et al. ............. 607/63 |
| 2011/0071599 A1 | 3/2011 | Olsen et al. |
| 2011/0071604 A1 | 3/2011 | Wahlstrand et al. |
| 2011/0106231 A1 | 5/2011 | Doan et al. |
| 2011/0112599 A1 | 5/2011 | Zhang et al. |
| 2011/0118813 A1 | 5/2011 | Yang et al. |
| 2011/0213445 A1 | 9/2011 | Blischak |
| 2011/0270369 A1 | 11/2011 | Tekmen et al. |

* cited by examiner

SECTION VIEW A-A"

SECTION VIEW A-A"

MR-COMPATIBLE IMPLANTABLE MEDICAL LEAD

This application claims the benefit of U.S. Provisional Application No. 61/717,462, filed on Oct. 23, 2012 and claims the benefit of U.S. Provisional Application No. 61/723,012, filed on Nov. 6, 2012. The entire content of both of these applications is incorporated herein by reference in their entirety.

TECHNICAL FIELD

The present disclosure relates to MR-compatible implantable medical leads.

BACKGROUND

In the medical field, implantable medical electrical leads are used with a wide variety of medical devices. For example, implantable medical electrical leads are commonly used to form part of an implantable medical system that provides therapeutic electrical stimulation to a patient, such as cardiac electrical stimulation to the heart in the form of pacing, cardioversion, defibrillation, or resynchronization pulses. The pulses can be delivered to the heart or other desired location within the patient via electrodes disposed on the leads, e.g., typically near distal ends of the leads. In that case, the leads may position the electrodes with respect to various locations so that the implantable medical system can deliver pulses to the appropriate locations. Leads are also used for sensing purposes, or for both sensing and stimulation purposes. Implantable leads are also used in neurological devices to deliver electrical stimulation to reduce the effects of a number of neurological disorders and in a number of other contexts.

Patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field may be generated by a primary magnet within the MRI device and may be present prior to initiation of the MRI procedure. The gradient magnetic fields may be generated by electromagnets of the MRI device and may be present during the MRI procedure. The RF fields may be generated by transmitting/receiving coils of the MRI device and may be present during the MRI procedure. If the patient undergoing the MRI procedure has an implantable medical system, the various fields produced by the MRI device may have an effect on the operation of the medical leads and/or the implantable medical device (IMD) to which the leads are coupled. For example, the gradient magnetic fields or the RF fields generated during the MRI procedure may induce energy on the implantable leads (e.g., in the form of a current), which may be conducted to tissue via the electrodes of the lead.

SUMMARY

An implantable medical lead may include components or mechanisms that can reduce the amount of induced current that is conducted to electrodes of the lead. This disclosure provides a medical lead(s) that include an energy dissipating structure that provides a second path in parallel with the electrical path from a coiled conductor to an electrode of the lead to redirect or shunt high frequency energy/signals away from the electrode. This disclosure provides techniques for electrically coupling the energy dissipating structure to the coiled conductor associated with the electrode.

In one example, this disclosure is directed to a medical electrical lead including a lead body having a proximal end configured to couple to an implantable medical device and a distal end, a conductive electrode shaft located near the distal end within the lead body, a coiled conductor extending within the lead body from the proximal end and coupled to a first end of the conductive electrode shaft, an electrode located near the distal end of the lead body and coupled to an opposite end of the conductive electrode shaft as the coiled conductor, and an energy dissipating structure located near the distal end of the lead body and formed from a conductive material that defines a lumen through which a portion of the coiled conductor extends. The portion of the coiled conductor extending through the lumen defined by the energy dissipating structure is formed to provide an interference contact with the energy dissipating structure.

In another example, this disclosure is directed to an implantable medical system comprising an implantable medical device and an implantable medical electrical lead. The implantable medical electrical lead includes a lead body having a proximal end configured to couple to the implantable medical device and a distal end, a conductive electrode shaft located near the distal end within the lead body, a coiled conductor extending within the lead body from the proximal end and coupled to a first end of the conductive electrode shaft, an electrode located near the distal end of the lead body and coupled to an opposite end of the conductive electrode shaft as the coiled conductor, and an energy dissipating structure located near the distal end of the lead body and formed from a conductive material that defines a lumen through which a portion of the coiled conductor extends. The portion of the coiled conductor extending through the lumen defined by the energy dissipating structure is configured to provide an interference contact with the energy dissipating structure that is substantially continuous.

In a further example, this disclosure is directed to a medical electrical lead including a lead body having a proximal end configured to couple to an implantable medical device and a distal end, an electrode located near the distal end of the lead body, a coiled conductor extending within the lead body from the proximal end and coupled to the electrode, and an energy dissipating structure located near the distal end of the lead body and formed from a conductive material that defines a lumen through which a portion of the coiled conductor extends, wherein the portion of the coiled conductor extending through the lumen defined by the energy dissipating structure is formed to provide an interference contact with the energy dissipating structure that is substantially continuous.

The portion of the coiled conductor extending through the lumen defined by the energy dissipating structure may be formed to have one or more sections having windings of a first outer diameter and one or more sections having windings of a second outer diameter, wherein the second outer diameter is greater than the first outer diameter and the sections having windings of the second outer diameter provide the interference contact with the energy dissipating structure. In one example, the lumen defined by the conductive material of the energy dissipating structure has an inner diameter and the second outer diameter of the sections of the coiled conductor may be approximately equal to the inner diameter of the lumen defined by the conductive material of the energy dissipating structure. In another example, the lumen defined by the conductive material of the energy dissipating structure has an inner diameter and the second outer diameter of the sections of the coiled conductor may be larger than the inner diameter of the lumen defined by the conductive material of the energy dissipating structure.

The coiled conductor may have a pre-formed geometry such that the portion of the coiled conductor extending through the lumen defined by the energy dissipating structure provides the interference contact with the energy dissipating structure. The portion of the coiled conductor extending through the lumen defined by the energy dissipating structure may be shaped into one of an arc and an undulated pattern. This may be a result of the pre-formed geometry or shape of the coiled conductor. The interference contact between the energy dissipating structure and the portion of the coiled conductor extending through the lumen defined by the energy dissipating structure may be substantially continuous during movement of the lead.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
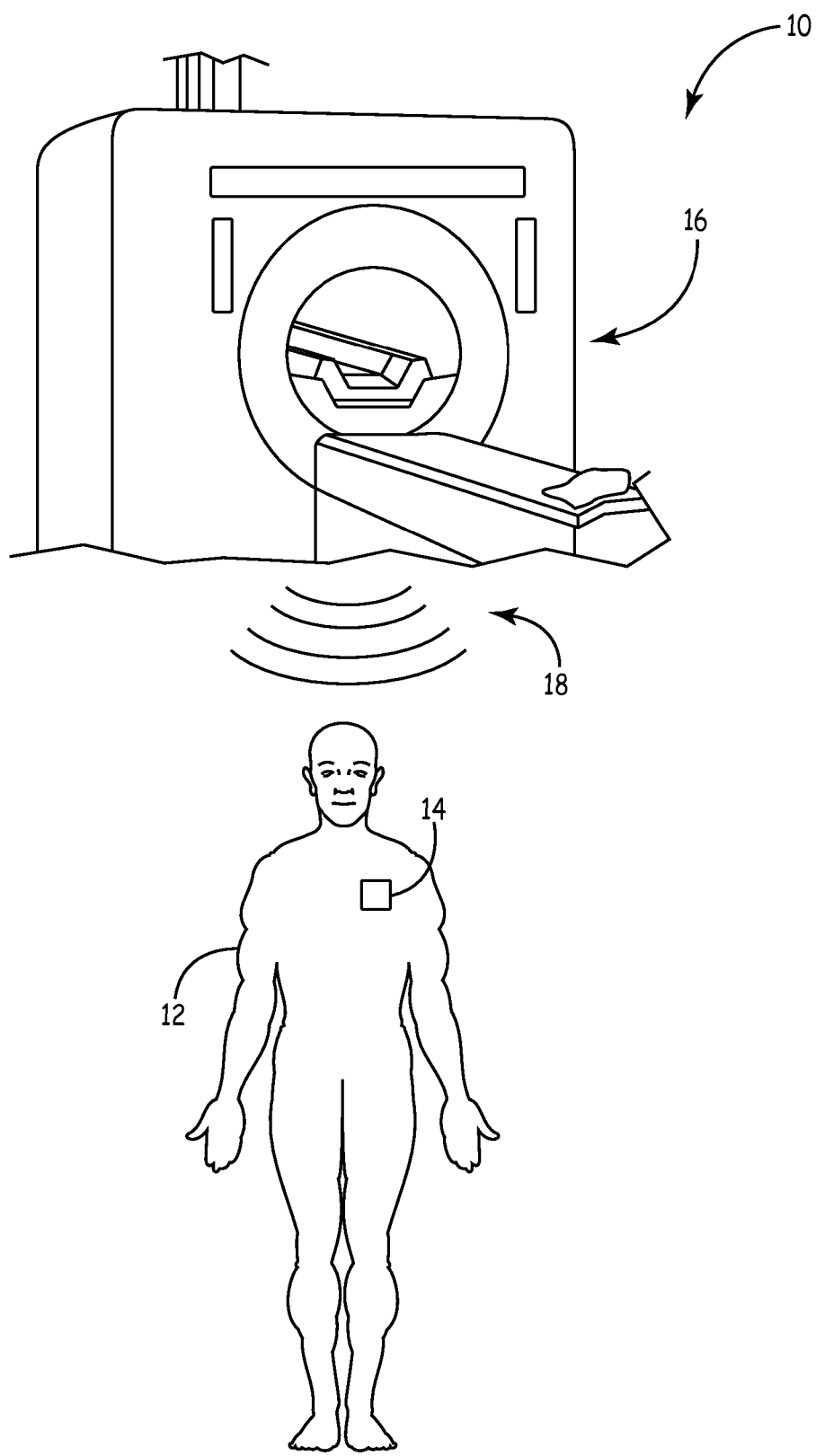
FIG. 1 is a conceptual diagram illustrating an environment in which a patient with an implantable medical system is exposed to external fields.

FIG. 1 is a conceptual diagram illustrating an environment 10 in which a patient 12 with an implantable medical system 14 is exposed to external fields 18. In the example illustrated in FIG. 1, environment 10 includes an MRI device 16 that generates external fields 18. MRI device 16 generates magnetic and RF fields to produce images of body structures for diagnosing injuries, diseases and/or disorders. In particular, MRI device 16 generates a static magnetic field, gradient magnetic fields and RF fields as is well known in the art. The static magnetic field is a non time-varying magnetic field that is typically always present around MRI device 16 whether or not an MRI procedure is in progress. Gradient magnetic fields are pulsed magnetic fields that are typically only present while the MRI procedure is in progress. RF fields are pulsed high frequency fields that are also typically only present while the MRI procedure is in progress.

The magnitude, frequency or other characteristic of the static magnetic field, gradient magnetic fields and RF fields may vary based on the type of MRI device producing the field or the type of MRI procedure being performed. For example, a 1.5 Tesla (T) MRI device will produce a static magnetic field of about 1.5 T and have a corresponding RF frequency of about 64 megahertz (MHz) while a 3.0 T MRI device will produce a static magnetic field of about 3.0 T and have a corresponding RF frequency of about 128 MHz. However, other MRI devices may generate fields of different strengths and/or frequencies Implantable medical system 14 may, in one example, include an implantable medical device (IMD) connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy.

Although environment 10 is described as including an MRI device 16 that generates external fields 18, environment 10 may include other sources of external fields 18, such as devices used for electrocautery procedures, diathermy procedures, ablation procedures, electrical therapy procedures, magnetic therapy procedures or the like. Moreover, environment 10 may include a non-medical source of external fields 18, such as an interrogation unit of a radio frequency (RF) security gate.

Figure 2:
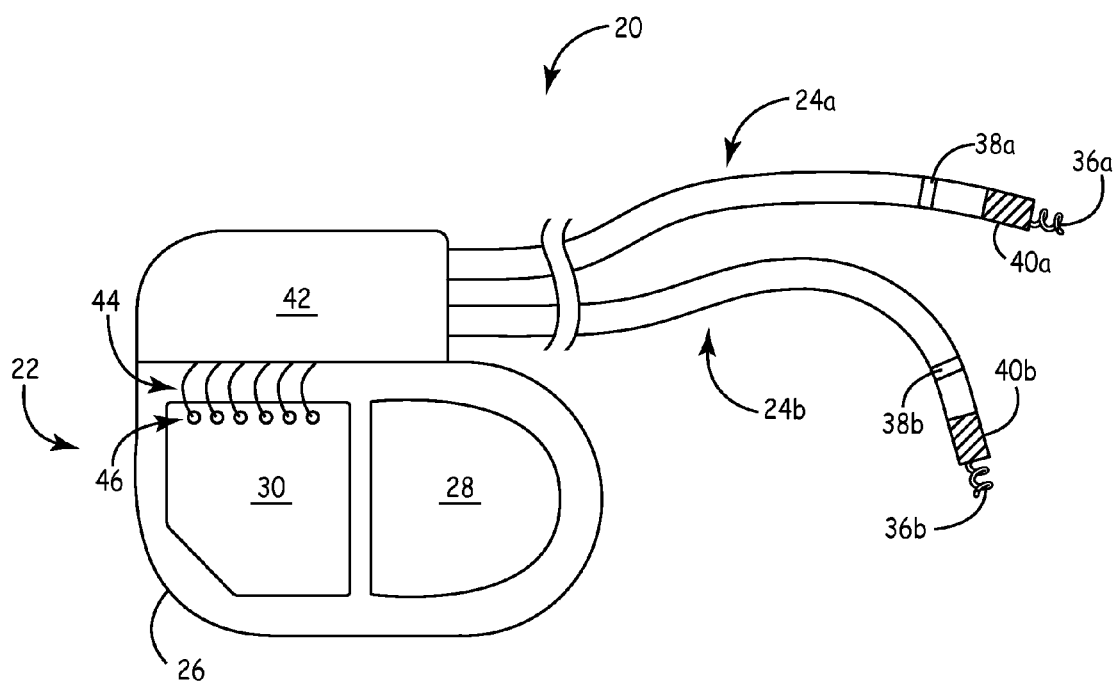
FIG. 2 is a schematic diagram illustrating an example implantable medical system.

FIG. 2 is a schematic diagram illustrating an example implantable medical system 20. Implantable medical system 20 may, for example, correspond with implantable medical system 14 of FIG. 1. Implantable medical system 20 includes an IMD 22 and leads 24a and 24b (sometimes referred to herein as leads 24 or leads 24a,b). IMD 22 may be an implantable cardiac device that senses electrical activity of a heart and/or provides electrical stimulation therapy to the heart. IMD 22 may, for example, be an implantable pacemaker, implantable ICD, implantable CRT-D, implantable cardioverter device, or other device or combinations thereof. IMD 22 may alternatively be a non-cardiac implantable device, such as an implantable neurostimulator or other device that provides electrical stimulation therapy.

IMD 22 includes a housing 26 within which components of IMD 22 are housed. Housing 26 can be formed from conductive materials, non-conductive materials or a combination thereof. IMD 22 includes a power source 28 and a printed circuit board (PCB) 30 enclosed within housing 26. Power source 28 may include a battery, e.g., a rechargeable or non-rechargeable battery, or other power source. PCB 30 includes one or more electrical components (not shown in FIG. 2) of IMD 22, such as one or more processors, memories, transmitters, receivers, sensors, sensing circuitry, therapy circuitry and other appropriate components.

PCB 30 may provide electrical connections between power source 28 and the electrical components of IMD 22 such that power source 28 powers the various electrical components of PCB 30. In some examples, PCB 30 may include one or more layers of conductive traces and conductive vias that provide electrical connection between power source 28 and the electrical components as well as provide electrical connections among the various electrical components. PCB 30 may not be limited to typical PCB structures, but may instead represent any structure within IMD 22 that is used to mechanically support and electrically connect the electrical components of IMD 22 and power source 28. Moreover, although the electronics components of IMD 22 are described as being on a single PCB, it is contemplated that the electronic components described herein may be included elsewhere within IMD 22, e.g., on other supporting structures within IMD 22, such as additional PCBs (not shown).

Leads 24*a,b* each include a respective tip electrode 36*a,b* and ring electrode 38*a,b* located near a distal end of respective leads 24*a,b*. In other examples, however, leads 24*a,b* may include more or fewer electrodes. When implanted, tip electrodes 36*a,b* and/or ring electrodes 38*a,b* are placed relative to or in a selected tissue, muscle, nerve or other location. In the example illustrated in FIG. 2, tip electrodes 36*a,b* are extendable helically shaped electrodes to facilitate fixation of the distal end of leads 24*a,b* to the target location within patient 12. In this manner, tip electrodes 36*a,b* are formed to define a fixation mechanism. In other embodiments, one or both of tip electrodes 36*a,b* may be formed to define fixation mechanisms of other structures. In other instances, leads 24*a,b* may include a fixation mechanism separate from tip electrode 36*a,b*. In this case, tip electrodes 36*a,b* may be passive, such as a hemispherical electrode or ring electrode. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

Leads 24*a,b* are connected at a proximal end to IMD 22 via connector block 42. Connector block 42 may include one or more ports that interconnect with one or more connector terminals located on the proximal end of leads 24*a,b*. Leads 24*a,b* are ultimately electrically connected to one or more electrical components on PCB 30 through, for example, connecting wires 44 that may extend within connector block 42. For example, connecting wires 44 may be connected to leads 24*a,b* at one end, and connected to PCB connection points 46 on PCB 30 at the other end.

One or more conductors (not shown in FIG. 2) can extend within a body of leads 24*a,b* from connector block 42 to engage the ring electrode 38*a,b* and tip electrode 36*a,b*, respectively. Each of the electrical conductors forms part of an electrical path from the proximal end of leads 24*a,b* to respective ones of electrodes 36*a,b* or 38*a,b*. The body of leads 24*a,b* may be formed from a non-conductive material, including silicone, polyurethane, fluoropolymers, mixtures thereof, and other appropriate materials, shaped to form a lumen within which the one or more conductors extend. In this manner, each of tip electrodes 36*a,b* and ring electrodes 38*a,b* is electrically coupled to a respective conductor within the lumen of the associated lead bodies. For example, a first electrical conductor can extend along the length of body of lead 24*a* from connector block 42 and electrically couple to tip electrode 36*a* and a second electrical conductor can extend along the length of the body of lead 24*a* from connector block 42 and electrically couple to ring electrode 38*a*. The respective conductors may couple to circuitry, such as a therapy module or a sensing module, of IMD 22 via connections in connector block 42, connecting wires 44 and PCB connection points 46. The electrical conductors conduct therapy generated by the therapy module within IMD 22 to combinations of electrodes 36*a,b* and 38*a,b* and transmit sensed electrical signals from electrodes 36*a,b* and 38*a,b* to the sensing module within IMD 22.

A patient having implanted medical system 20 may receive a certain therapy or diagnostic technique, surgery, or other procedure that exposes implantable medical system 20 to external fields, such as external fields 18 of FIG. 1. In the case of an MRI procedure, for example, implantable medical system 20 is exposed to high frequency RF pulses and various magnetic fields to create image data regarding the patient 12. The RF pulses can induce currents within the leads 24*a,b* of the IMD 22, e.g., on the conductors of leads 24*a,b*. The current induced in the leads 24*a,b* can cause certain effects, including heating, of the various lead components and/or tissue near the lead. According to various embodiments, such as those discussed herein, components or mechanisms can be provided to reduce or eliminate the amount of current at tip electrodes 36*a,b* and/or ring electrodes 38*a,b*.

According to various embodiments discussed herein, one or both of leads 24*a,b* include components or mechanisms to reduce or eliminate the amount of current induced by external fields. To this end, each of leads 24*a,b* includes a respective energy dissipating structure 40*a,b* that functions as a shunt to redirect at least a portion of the current induced on leads 24*a,b* is redirected. In one example, energy dissipating structures 40*a,b* are coupled to the conductors that form part of the electrical path from the proximal end of leads 24*a,b* to tip electrodes 36*a,b*. In this manner, energy dissipating structures 40*a,b* provide a second electrical path that is in parallel with the electrical path through respective tip electrodes 36*a, b*. Energy dissipating structures 40*a,b* are designed to present low impedances at high frequencies, such as those frequencies produced by MRI device 16, thereby redirecting a significant amount of current induced by the high frequency signals from the first electrical paths through tip electrodes 36*a,b* to the second electrical paths through energy dissipating structures 40*a,b*.

Redirecting or shunting at least a portion of the induced current from tip electrodes 36*a,b* to energy dissipating structures 40*a,b* increases the area over which the current or thermal energy is dissipated, thereby decreasing the amount of heating adjacent to tip electrodes 36*a,b*. Energy dissipating structures 40*a,b* may, for example, comprise a conductive housing, a ring electrode, a sheath, a sleeve head, or an electrically and thermally conductive material. In this manner, the medical electrical leads described in this disclosure may allow a patient to undergo medical procedures that utilize high frequency signals without significantly affecting operation of the implantable medical system.

The conductors, and particularly the conductor associated with tip electrodes 36*a,b*, may be a coiled conductors formed from one or more wire filars wound to form the coiled conductor. These coiled conductors have inherent spring properties due to the fact that they are formed by winding the one or more wire filars. The inherent spring properties of the coiled conductors may be used to achieve an interference contact between the coiled conductors and energy dissipating structure 40. For example, the inherent spring properties that are present in lead coiled conductors along with a geometry of either the energy dissipating structure 40, a distal sleeve head, and/or the coiled conductor itself allow the coil to maintain contact with the energy dissipating structure 40 or connection component coupled to the energy dissipating structure.

Energy dissipating structures 40*a,b* may be coupled to the conductors via a number of different mechanisms described in this disclosure. In one example, an inner geometry of a portion of energy dissipating structures 40*a,b* may be formed to contact the conductors and force the portion of the conductors extending through energy dissipating structures 40*a,b* off center. In other words, the geometry of the inner surface of energy dissipating structures 40*a,b* may cause the conductors extending through that portion to follow an undulated, sinusoidal, or helical sweep path. In another example, the conductors may be coupled to the energy dissipating structures 40*a,b* by shifting the conductor axis near a distal end of the lead off center via a lumen position change within the lead or within the distal sleeve heads. In a further embodiment, the conductors themselves may be modified in the vicinity of the energy dissipating structure 40*a,b* to couple to the energy dissipating structures 40*a,b*. Each of these examples, which will be described in more detail in the subsequent figures, provides an interference contact using the inherent spring properties of the coiled conductors, thereby providing a consistent, low cost connection between the conductor and the energy dissipating structures 40*a,b*. Moreover, in some instances, the connection between the conductor and the energy dissipating structures 40*a,b* is made without relying on separate connection components.

The embodiments described in this disclosure are generally discussed in the context of reducing induced current to tip electrodes 36*a,b*. However, this disclosure is not limited to such embodiments. One of skill in the art would understand that modifications may be made to reduce the amount of induced current conducted to ring electrodes 38*a,b* in addition to or instead of tip electrodes 36*a,b*. As such, the configuration of implantable medical system 20 of FIG. 2 is merely an example. Modifications may be made while still remaining within the scope of this disclosure.

The techniques of this disclosure may be used with leads have a coaxial, co-radial (or isodiametric), multi-lumen or other lead design. In some examples, implantable medical system 20 may include more or fewer leads extending from IMD 22. For example, IMD 22 may be coupled to three leads, e.g., implanted within the right atrium, right ventricle and left ventricle of the heart. In another example, IMD 22 may be coupled to a single lead that is implanted within either an atrium or ventricle of the heart. As such, implantable medical system 20 may be used for single chamber or multi-chamber cardiac rhythm management therapy.

In addition to more or fewer leads, each of the leads 24 may include more or fewer electrodes. In instances in which IMD 22 is used for therapy other than pacing, e.g., defibrillation or cardioversion, the leads may include elongated electrodes, which may, in some instances, take the form of a coil. IMD 22 may deliver defibrillation or cardioversion shocks to the heart via any combination of the elongated electrodes and housing electrode. As another example, medical system 20 may include leads with a plurality of ring electrodes, e.g., as used in some implantable neurostimulator, with a conductor associated with each of the plurality of ring electrodes and having one or a plurality of lumens.

Figure 3:
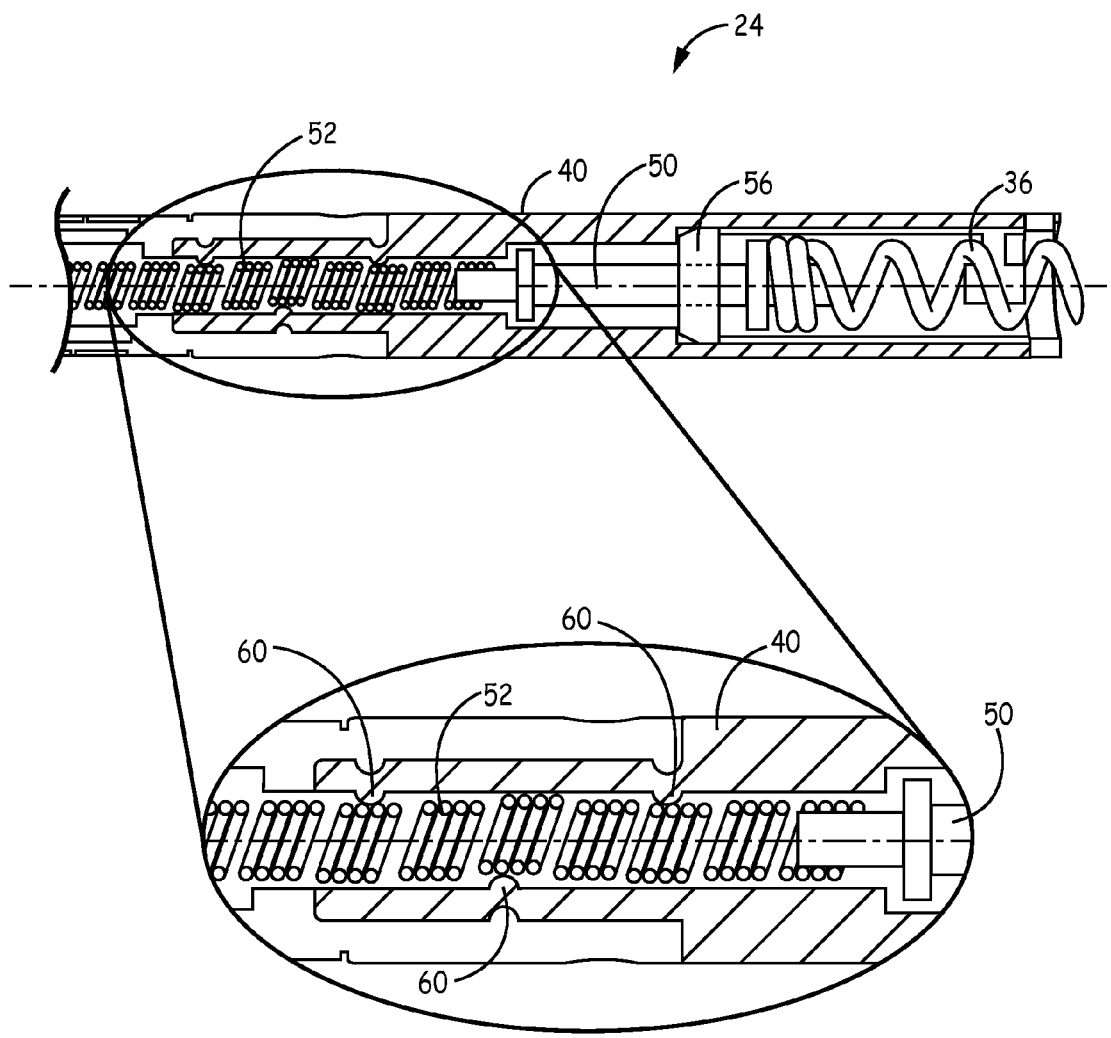
FIG. 3 is a schematic diagram illustrating a longitudinal cross-sectional view of a distal end of a lead.

FIG. 3 is a schematic diagram illustrating a longitudinal cross-sectional view of a distal end of a lead 24. Lead 24 may correspond with lead 24*a* or lead 24*b* of FIG. 2. Lead 24 includes a tip electrode 36 and possibly a ring electrode (not shown). Tip electrode 36 may be electrically coupled to one or more electronic components on PCB 30 of IMD 22 via an electrical path that exists from a proximal end of lead 24 (which is coupled to connector block 42 of IMD 22) to tip electrode 36. In the example illustrated in FIG. 3, the electrical path from the proximal end of lead 24 to tip electrode 36 includes a coiled conductor 52 and an electrode shaft 50.

In the example illustrated in FIG. 3, electrode shaft 50 is connected at one end to coiled conductor 52 and at the other end to tip electrode 36. Electrode shaft 50 may be connected to coiled conductor 52 and tip electrode 36 via welding, soldering, crimping or other connection mechanism. Coiled conductor 52, electrode shaft 50 and tip electrode 36 may all be formed at least partially from a conductive material, such as titanium, titanium alloy, tantalum, tantalum alloy platinum, platinum iridium, conductive polymers, and/or other suitably conductive material or combination of materials. Coiled conductor 52, electrode shaft 50 and tip electrode 36 may be all formed of the same conductive material or different conductive materials. In one example, coiled conductor 52 is a multi-filar coil having a plurality of co-radially wound wire filars.

The mechanical coupling of coiled conductor 52, electrode shaft 50 and tip electrode 36 provides a mechanical relationship that may, in some instances, allow for mechanical control of tip electrode 36 such that it may be extended from and retracted within the distal end of lead 24. During implantation, for example, a physician or other user may interact with lead 24 to rotate coiled conductor 52, which causes electrode shaft 50 to rotate and extend/retract tip electrode 36 from the distal end of lead 24. In this manner, tip electrode 36 may be screwed into the target tissue location. As such, coiled conductor 52 may have sufficient rigidity to assist in attaching tip electrode 36 to the target tissue location while being flexible enough to navigate through body lumens, e.g., through one or more veins. In other examples, tip electrode 36 may be extended/retracted via a translational force instead of a rotational force. In other instances, electrode shaft 50 may be formed to receive a stylet to guide lead 24 during implantation or to allow a user to extend and/or retract tip electrode 36. In further instances, lead 24 may not include an electrode shaft 50. Instead, conductor 52 may be directly connected to tip electrode 36 and may or may not allow for mechanical control of tip electrode 36

As described above, certain therapy or diagnostic techniques, such as an MRI procedure, may expose lead 24 to high frequency RF pulses and magnetic fields. Additionally, certain non-medical environments may also include RF fields to which lead 24 is exposed. The RF pulses can induce currents on conductor 52 within lead 24 of the IMD 22. The induced current on conductor 52 may be conducted to tip electrode 36. Lead 24 includes components or mechanisms that can reduce the amount of induced current that is conducted to tip electrode 36. Although described in the context of reducing current to tip electrode 36, lead 24 may include similar mechanism or other mechanisms that may reduce the induced current conducted to ring electrodes in addition to tip electrodes 36.

Lead 24 of FIG. 3 includes an energy dissipating structure 40 that is electrically coupled to the electrical path from the proximal end of lead 24 to tip electrode 36 near the distal end of lead 24. In particular, energy dissipating structure 40 is electrically coupled to coiled conductor 52 near the distal end of lead 24 to provide a second electrical path through energy dissipating structure 40 that is in parallel with the electrical path through tip electrode 36.

Energy dissipating structure 40 presents a high impedance at low frequencies, such as those frequencies used for pacing or other stimulation therapies (e.g., ~1 kHz for pacing signals). As such, only a small amount of current is redirected away from tip electrode 36, e.g., along the second electrical path to energy dissipating structure 40, at low frequencies. In this manner, energy dissipating structure 40 functions as a shunt for high frequency energy by essentially having electrical isolation at low pacing frequencies allowing pacing to occur at the tip electrode surface. Energy dissipating structure 40 presents a low impedance at high frequencies, such as those frequencies produced by MRI device 16 (greater than 1.0 MHz), resulting in a significant amount of the induced current being redirected away from the first electrical path through tip electrode 36 to the second electrical path through energy dissipating structure 40. Thus, energy dissipating structure 40 functions by coupling a significant amount of the higher frequency energy through the energy dissipating structure 40. In one example, an electrical lead with an energy dissipating structure 40 as described herein may result in at least 50% of the energy induced by high frequency RF signals of an MRI device to be redirected away from tip electrode 36 while less than 10% of the energy associated with a pacing therapy is directed through energy dissipating structure 40.

In some instances, energy dissipating structure 40 has a surface area that is significantly larger than a surface area of tip electrode 36. The surface area of energy dissipating structure 40 may, in one example, be between approximately 20-100 mm$^2$, which is at least approximately ten times larger than the surface area of tip electrode 36. A large surface area ratio, defined by the ratio of the surface area of energy dissipating structure 40 to the surface area of tip electrode 36 is desired to dissipate the induced current over a larger area to reduce heating at any specific location.

Energy dissipating structure 40 may include a conductive material that is at least partially covered by a layer of insulating material. In one example, the insulation material may cover at least the portion of energy dissipating structure 40 that is exposed to the bodily fluid and/or tissue of patient 12 such that the outer surface of the conductive material of energy dissipating structure 40 does not contact a body of the patient when implanted. In other instances, however, conductive material of energy dissipating structure 40 may be directly exposed to bodily fluid and/or tissue, i.e., not include the layer of insulating material. Conductive material may be an electrically and thermally conductive material, such as titanium, titanium alloy, tantalum, tantalum alloy, platinum, platinum iridium, conductive polymers, nickel-cobalt alloy (e.g., MP35N®) and/or other suitably conductive material or combination of materials.

The insulating material may cover an outer surface of conductive material or at least a portion of the outer surface of conductive material. Insulating material may affect the impedance of energy dissipating structure 40 and reduce the effect of energy dissipating structure 40 on the tip electrode to tissue interface impedances. As the thickness of insulating material increases, the capacitance associated with energy dissipating structure 40 decreases and the impedance of energy dissipating structure 40 increases. As a result the amount of current redirected to energy dissipating structure 40 is reduced, but there is less interference with therapy delivered by IMD 22. As the thickness of insulating material 64 decreases, the capacitance associated with energy dissipating structure 40 increases and the impedance of energy dissipating structure 40 decreases. As a result the amount of current (even at low frequencies) redirected to energy dissipating structure 40 is increased, which may affect therapy delivered IMD 22.

For example, an energy dissipating structure 40 having a surface area of approximately 22 square millimeters (mm$^2$) and an insulating material having a dielectric constant of approximately 4.0, an insulating material thickness of approximately 68 micrometers provides an impedance of approximately 10 Ohms and a capacitance of approximately 250 pF, a thickness of approximately 34 micrometers provides an impedance of approximately 5 Ohms and a capacitance of approximately 500 pF, and a thickness of approximately 17 micrometers provides an impedance of approximately 2.5 Ohms and a capacitance of approximately 1 nF. These values are only exemplary in nature. The electrical characteristics of energy dissipating structure 40 may take on different values depending on the construction of the distal end of lead 24, e.g., based on the surface area of tip electrode 36, the surface area of energy dissipating structure 40, the thickness of insulating material, the material from which the various components are constructed, and the like.

The thickness of insulating material may be selected by a therapy system/lead designer to achieve a satisfactory tradeoff between capacitance and impedance. Numerous techniques may be employed to introduce insulating material over the outside of energy dissipating structure 40 and/or partially inside energy dissipating structure 40. Exemplary techniques include anodizing, chemical vapor deposition, dip layer, spraying, thermal reflow, or thermal extrusion or molding.

Insulating material may also cover at least a portion of an inner surface of conductive material. Insulating material on the inner surface may prevent conductive material of energy dissipating structure 40 from making direct contact with the conductive material of tip electrode 36, electrode shaft 50 and/or coiled conductor 52 at locations other than desired. In some instances, the insulating material may even cover the surface of the portion of conductive material contacting coiled conductor 52. In this case, the coupling between energy dissipating structure 40 and coiled conductor 52 is a non-conductive (e.g., capacitive or thermal) coupling instead of a conductive coupling. In some instances, energy dissipating structure 40 may include more than one layer of insulating material, with each layer being made of the same or different insulating material. Insulating material may include parylene, metal oxides, polyimide, urethane, silicone, tetrafluroethylene (ETFE), polytetrafluoroethylene (PTFE), polyether ether ketone (PEEK), oxides, or other suitable non-conductive material or combination of materials.

It is desirable that the contact between energy dissipating structure 40 and coiled conductor 52 is continuous, as intermittent metal-metal contact of coiled conductor 52 and energy dissipating structure 40 may generate electrical noise. Moreover, with extendable\retractable leads this electrical connection/contact, the tip electrode 36 (which may be a helix as illustrated in FIG. 3) and inner circuit (which may include coiled conductor 52 and electrode shaft 50) may rotate while the energy dissipating structure 40 remains fixed. It is thus desirable to have an electrical connection/contact that reduces the effect on lead extension performance while maintaining constant contact and presents a low resistance connection during MRI procedures. It may also be desirable to have the connection/contact mitigate electrical noise that could be generated via by intermittent metal-metal contact of inner circuit and energy dissipating structure 40 or by this electrical connection. Noise generated by intermittent contact could present itself as cardiac signals since the lead tip is moving at the same rate as the heart in some cardiac implementations. To help mitigate this noise potential the energy dissipating structure 40 can be completely isolated with the exception of this electrical connection and/or this electrical connection need to be of low enough resistance to drain off/ground the metal components resting potential such that noise is minimized by metal to metal contact.

Past solutions have been to make springs, spring clips, conductive seals, or the like that will make these electrical connections. These options require that separate component(s) be added that makes contact with electrode shaft 50. Some of these solutions may utilize components that are constructed of a material that is harder than that of electrode shaft 50 (which may be constructed of materials such as platinum/iridium (Pt/Ir)) so that the electrical connection component will not easily plastically deform and will maintain spring properties during assembly and use. The softer material of electrode shaft 50 may, in some instances, be subject to galling when used in combination with harder spring materials. Additionally, the smaller sizes and tolerances of the springs, spring clips, conductive seals, or the like, make these components difficult and/or expensive to manufacture.

In accordance with one aspect of this disclosure, lead 24 may be formed to make electrical connection directly between coiled conductor 52 and energy dissipating structure 40 by way of an interference contact. In the example of FIG. 3, the inherent spring properties that are present in lead coils, such as coiled conductor 52, along with a geometry of energy dissipating structure 40 allow the coiled conductor 52 to maintain constant electrical contact with energy dissipating structure 40 and provide a consistent, low cost electrical connection directly between the coiled conductor 52 and the energy dissipating structure 40.

In the example illustrated in FIG. 3, the conductive material of energy dissipating structure 40 defines a lumen through which a portion of coiled conductor 52 extends. Energy dissipating structure includes a region having a plurality of protrusions 60 extending from an inner surface toward a central axis of the lumen defined by energy dissipating structure 40. Protrusions 60 contact portions of coiled conductor 52 that extend through that portion of the energy dissipating structure 40 to slightly force coiled conductor 62 off center in multiple locations relative to a central axis of the lumen formed by the energy dissipating structure. In this manner, protrusions 60 push portions of the coiled conductor 52 off center relative to the central axis such that coiled conductor follows a slightly undulated, sinusoidal, or helical sweep path through the portion of energy dissipating structure 40 having the plurality of protrusions 60.

The natural response of coiled conductor 52, which has many inherent properties similar to a spring, is to realign such that the coiled conductor 52 is no longer off center thus exerting a force against protrusions 60. The force provides an electrical connection achieved by the friction between the coiled conductor 52 and energy dissipating structure 40. In this manner, the interference contact is accomplished using the inherent spring properties of coiled conductor 52 and the geometry (formed by protrusions 60) of the inner surface of energy dissipating structure 40.

The spacing between subsequent protrusions 60 along the length of energy dissipating structure 60 may affect the extension/retraction capabilities of lead 24. It may be desirable to space protrusions 60 (or sets of protrusions 60) along the longitudinal length of energy dissipating structure 40 such that none of protrusions 60 contact substantially opposite sides of coiled conductor 52 within one and one-half (1½) turns of coiled conductor 52. Such spacing may be of particular interest in active fixation leads in which rotation of the coiled conductor 52, electrode shaft 50, and/or tip electrode 36 relative to the rest of the lead 24 is desirable. In fact, depending on the desired handling and extension/retraction characteristics, the spacing of protrusions may be larger, e.g., such that none of protrusions 60 contact substantially opposite sides of coiled conductor 52 within two or more turns of coiled conductor 52. The spacing between protrusions 60 (or sets of protrusions 60) along the longitudinal length of energy dissipating structure 40 may also be less than that described above in some instances. In the case of passive fixation leads, in which rotation of the coiled conductor 52, electrode shaft 50, and/or tip electrode 36 relative to the rest of the lead 24 is not necessary, a smaller spacing between protrusions along the longitudinal length of energy dissipating structure 40 of less than one and one-half turns may be used.

Additionally, the size and depth of protrusions 60 may affect the resistance of energy dissipating structure 60, affect how much coiled conductor 52 is off center and thereby how much force is exerted by coiled conductor 52 on protrusions 60, affect the extension/retraction capabilities of lead 24, and the like. As such, the size and depth of protrusions 60 may be formed such that force exerted against protrusions 60 are sufficient to maintain contact with energy dissipating structure 40 during flexing and other movement of lead 24, but still allow coiled conductor 52 to rotate and turn and allow a stylet to pass without significant interference of the stylet.

In the case of an active fixation lead, it may be desirable that protrusions 60 do not push coiled conductor 52 so far off center that it contacts the portion of energy dissipating structure 40 substantially opposite of protrusions 60. In the example illustrated in FIG. 3, at least some space still exists between coiled conductor 52 and the portion of energy dissipating structure 40 substantially opposite protrusions 60. In other instances (such as passive fixation leads and possibly active fixation lead), some contact may occur, but the contact cannot interfere with the rotation of coiled conductor 52 and tip electrodes 36.

In the example illustrated in FIG. 3, protrusions 60 are hemispherical bumps that extend inward from the inner surface of energy dissipating structure 40. However, in other example, protrusions 60 may be made in different shapes including rectangular notches, square notches, oval notches, and the like. Protrusions 60 may be generated by crimping, staking, machining, molding, forming or other technique.

Lead 24 may also include a seal 56. Seal 56 may be in contact with energy dissipating structure 40 and electrode shaft 50 to obstruct fluid from passing into the lumen defined by the body of the lead. Seal 56 may be substantially ring (e.g. o-ring) or disk shaped but other suitable shapes may also be employed. In one example, seal 56 may be a non-conductive sealing washer or a conductive sealing washer with a non-conductive coating. Lead 24 may also include one more rings that may hold seal 56 in place. In some instances, energy dissipating structure 40 and/or electrode shaft 50 may also be in contact with rings. Rings may, in one example, be shaped as a non-conductive C-ring to receive seal. However, rings of other shapes may be used. In further instances, lead 24 may not include any rings or seal 56.

Figure 4A:
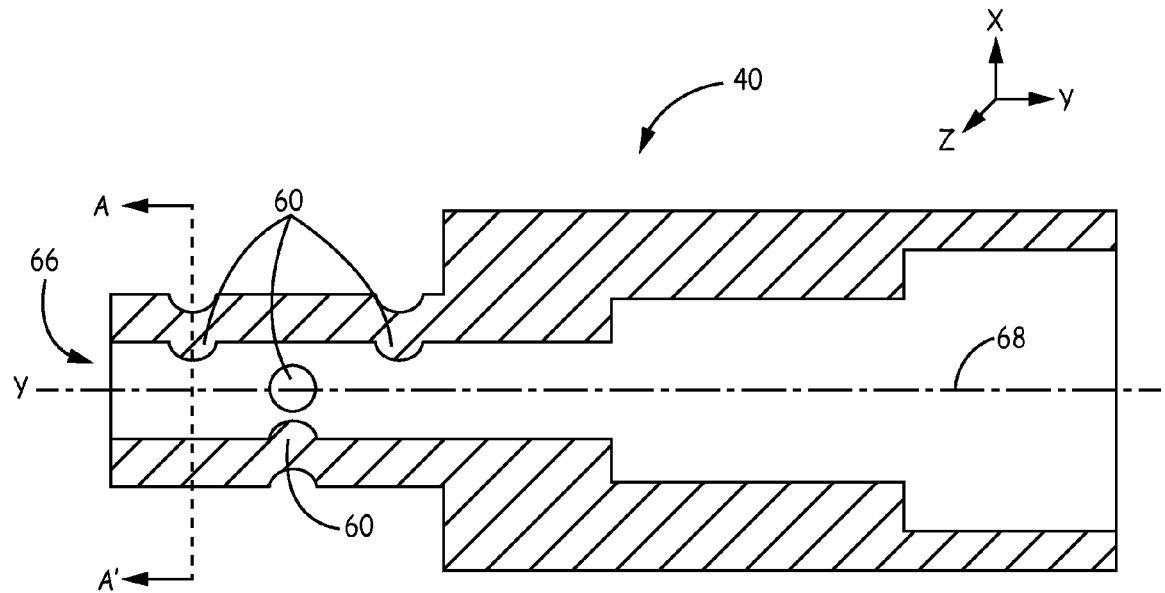
FIGS. 4A-4C illustrate various views of an example energy dissipating structure in further detail.
Figure 4B:
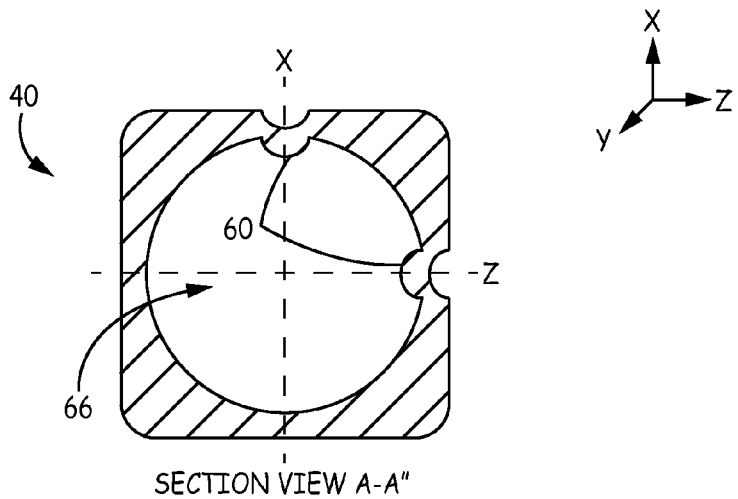
Figure 4C:
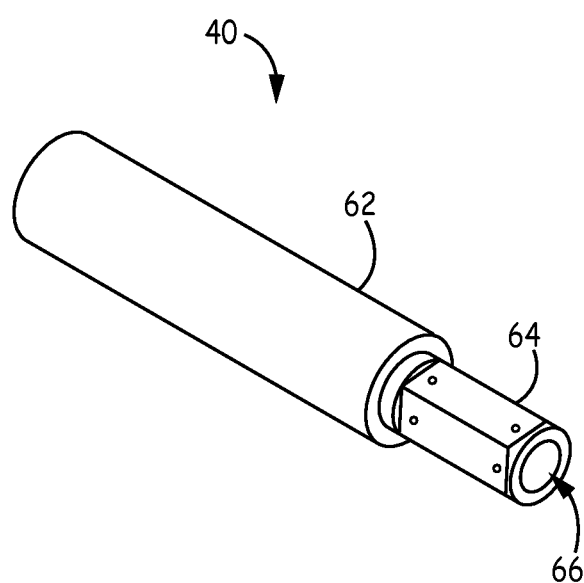

FIGS. 4A-4C illustrates various views of energy dissipating structure 40 of FIG. 3 in further detail. FIG. 4A illustrates a longitudinal cross-sectional view of energy dissipating structure 40. FIG. 4B illustrates a section view of energy dissipating structure 40 from A-A'. FIG. 4C is an angled view of energy dissipating structure 40.

Energy dissipating structure 40 defines a lumen 66 through which, as illustrated in FIG. 3, a portion of coiled conductor 52 extends. Energy dissipating structure 40 includes a region having a plurality of protrusions 60 extending toward a central axis 68 of lumen 66 defined by energy dissipating structure 40. As illustrated in FIG. 4A, pairs of protrusions 60 are separated from one another along a longitudinal length of the inner surface of energy dissipating structure 40. In the illustrated example, protrusions 60 are located at three cross-sectional locations along the longitudinal length of energy dissipating structure 40 (best illustrated in FIG. 4A). In other instances, however, protrusions may be located at more or less than three cross-sectional locations along the longitudinal length of energy dissipating structure 40.

Energy dissipating structure 40 further includes more than one protrusion 60 along the circumference of the inner surface of the energy dissipating structure 40 at each of the cross-sectional locations. In the example illustrated in FIGS. 4A and 4B, for example, energy dissipating structure 40 has a first set (or pair) of protrusions 60 at 0 degree and 90 degree positions in the x-z plane at the first cross-sectional location, a second set (or pair) of protrusions 60 at 180 degree and 270 degree positions in the x-z plane at the second cross-sectional location, and a third set (or pair) at the 0 degree and 90 degree positions in the x-z plane at the third cross-sectional location. FIG. 4B illustrates the cross sectional view from A-A', which includes the first set (or pair) of protrusions 60 that are located at approximately the 0 degree and 90 degree positions in the x-z plane. In other examples, energy dissipating structure 40 may include only a single protrusion 60 at each of the cross-sectional locations or the protrusions may be separated by varying degrees (e.g., greater than or less than 90 degrees).

As described above with respect to FIG. 3, protrusions 60 contact portions of coiled conductor 52 that extend along that portion of the energy dissipating structure 40 to slightly force coiled conductor 62 off center in multiple locations relative to a central axis of the lumen defined by energy dissipating structure 40. In this manner, protrusions 60 push portions of the coil off center relative to the central axis such that coiled conductor follows a slightly undulated, sinusoidal, or helical sweep path through the portion of energy dissipating structure 40 having the plurality of protrusions 60. In the example of FIGS. 4A and 4B, the first pair of protrusions 60 in the first cross-sectional location push coiled conductor 52 downward and into of the page (e.g., along the x- and z-axis), the second pair of protrusions 60 in the second cross-sectional location push coiled conductor 52 upward and out of the page (e.g., in approximately the opposite direction along the x- and z-axis), and the third pair of protrusions 60 in the third cross-sectional location push coiled conductor 52 upward and out of the page (e.g., along approximately the same x- and z-axis as the first pair of protrusions).

The result is that coiled conductor 52 extends along a slightly sinusoidal, undulated or helical sweep path. The inherent spring properties of coiled conductor 52 exert a force against protrusions 60 to achieve an interference connection between the coiled conductor 52 and energy dissipating structure 40. In this manner, the interference contact or connection is accomplished using the inherent spring properties of coiled conductor 52 and the geometry (formed by protrusions 60) of the inner surface of energy dissipating structure 40. Protrusions are formed such that the force exerted against protrusions 60 are sufficient to maintain contact with energy dissipating structure 40 during flexing and other movement of lead 24, but still allow coiled conductor 52 to rotate and turn and allow a stylet to pass without significant interference of the stylet.

Each of protrusions 60 contact one or more of the filars of coiled conductor 52. The number of protrusions 60, dimensions of protrusions 60, and spacing between protrusions 60 along both the length and inner circumference may be designed to provide adequate contact with coiled conductor 52 without significantly affecting the extension and retraction capability of coiled conductor 52. For example, the longitudinal length of protrusions 60 may be formed to come into contact with multiple filars of coiled conductor 52. This, in effect, provides increased contact points at each interface between energy dissipating structure 40 and coiled conductor 52 since each of the filars of coiled conductor 50 is independent. Additionally, the length of individual protrusions 60 may be formed to prevent protrusions 60 from pushing, extending or otherwise dropping between filars of coiled conductor 52. For example, the length of protrusions 60 may be greater than the diameter of a single filar of the multi-filar lead. The length of protrusions 60 may, for example, be approximately equal two times, three times, or four times the diameter of a single filar. As such, each of protrusions 60 makes contact with more than one filar of a multi-filar conductor. For a multi-filar coil having a wire size of 0.005 diameter, protrusions 60 may have a length of approximately 0.010. In some instances, protrusions 60 may be spaced to contact different ones of the filars of coiled conductor 52. In this manner, protrusions 60 may bridge the filars of coiled conductor 52 for a smoother extension/retraction.

The depth of protrusions 60, e.g., the distance from the inner surface of energy dissipating structure 40 to the portion of protrusions 60 located closest to the central axis of the lumen defined by energy dissipating structure 40, may also be designed to achieve particular characteristics. In the case of an active fixation lead, for example, it may be desirable that the protrusions do not push coiled conductor 52 so far off center that it contacts the portion of energy dissipating structure 40 opposite of protrusions 60. In other instances (such as passive fixation leads and possibly active fixation lead), some contact may occur between coiled conductor 52 and non-protrusion portions of energy dissipating structure 40, but the contact should not interfere with the rotation of coiled conductor 52, electrode shaft 50, and/or tip electrodes 36. In other words, it is undesirable to have protrusions 60 that are thick or deep enough to pinch, crush, or otherwise exert too much force on coiled conductor 52 such that extension and retraction of tip electrode 36 is affected.

Additionally, protrusions 60 (or sets of protrusions 60) may be spaced apart from one another along the longitudinal length of energy dissipating structure 40 such that contact from subsequent protrusions does not inhibit the extension/retraction capabilities. In the example construction illustrated in FIGS. 3 and 4 in which subsequent sets of protrusions 60 are located in locations substantially opposite from the previous set of protrusions 60 (e.g., the first set (or pair) of protrusions 60 located 0 degree and 90 degree positions in the x-z plane at the first cross-sectional location and the second set (or pair) of protrusions 60 at 180 degree and 270 degree positions in the x-z plane at the second cross-sectional location), it may be desirable to space sets of protrusions 60 along the longitudinal length of energy dissipating structure 40 by at least one and one-half (1½) turns of coiled conductor 52. In this manner, coiled conductor 52 has traveled at least one and one-half turns before any protrusions contact the filars of coiled conductor 52 on substantially opposite sides of coiled conductor 52. In other words, it may be desirable that no subsequent protrusions contact the opposite side of coiled conductor as a previous protrusion until the coiled conductor 52 has extended at least one and one-half turns.

Such spacing may be of particular interest in active fixation leads in which rotation of the coiled conductor 52, electrode shaft 50, and/or tip electrode 36 relative to the rest of the lead 24 is desirable. In fact, depending on the desired handling and extension/retraction characteristics, the spacing of protrusions may be larger, e.g., such that none of protrusions 60 contact substantially opposite sides of coiled conductor 52 within two or more turns of coiled conductor 52. The spacing between protrusions 60 (or sets of protrusions 60) along the longitudinal length of energy dissipating structure 40 may also be less than that described above in some instances. In the case of passive fixation leads, in which rotation of the coiled conductor 52, electrode shaft 50, and/or tip electrode 36 relative to the rest of the lead 24 is not necessary, a smaller spacing between protrusions along the longitudinal length of energy dissipating structure 40 of less than one and one-half turns may be used.

The example illustrated in FIGS. 4A-4C illustrates one example configuration of energy dissipating structure 40. As described above, however, energy dissipating structure 40 may be designed to include more or fewer protrusions having different shapes and being located in different locations without departing from the scope of this disclosure. For example, energy dissipating structure 40 may include protrusions located at three cross-sectional locations along the longitudinal length with only one protrusion at each of the cross-sectional locations. In this alternate example, the protrusions may push the coil in opposite directions at each subsequent cross-sectional location such that coiled conductor 52 follows a sinusoidal or undulated path or the protrusions may be arranged to be 90 degrees relative to one another (or some other angle relative to one another) such that coiled conductor 52 follows some sort of helical sweep path.

FIG. 4C illustrates an angled view of energy dissipating structure 40. Energy dissipating structure 40 may have at least two sections that having different outer diameters. For example, a first section 62 of energy dissipating structure 40 has an outer diameter that is approximately equal to the outer diameter of lead 24 such that it is exposed to the body of patient 12 and a second section 64 of energy dissipating structure 40 has an outer diameter that is less than the outer diameter of lead 24.

In the example illustrated in FIG. 4C, first section 62 has a generally cylindrical shape and second section 64 has more of a rectangular shape. Such a construction may provide additional stability of first section 62 when protrusions 60 are being formed via crimping, pressing, staking, or other similar technique. In other instances, the protrusions may be formed via machining or forming of energy dissipating structure. In these instances, the use of a generally cylindrical geometry may be sufficient.

In some instances a kerf, groove or notch may be formed (e.g., via laser or other mechanism) in the region of energy dissipating structure 40 including protrusions 60. The kerf, groove or notch would allow that region of energy dissipating structure 40 to bend or flex slightly allowing for more intimate contact when the lead moves. The kerf, groove or notch may be formed on an outer surface of the region of energy dissipating structure 40 including protrusions 60. In one example, the kerf, groove or notch may be formed helically along the portion of energy dissipating structure 40 including protrusions 60. In other instances, the kerf, groove, or notch may take other shapes and arrangements, such as a plurality of kerfs, grooves or notches extending around the outer circumference of energy dissipating structure 40 and spaced apart from one another along the longitudinal length of the region of energy dissipating structure 40 having protrusions 60.

Figure 5A:
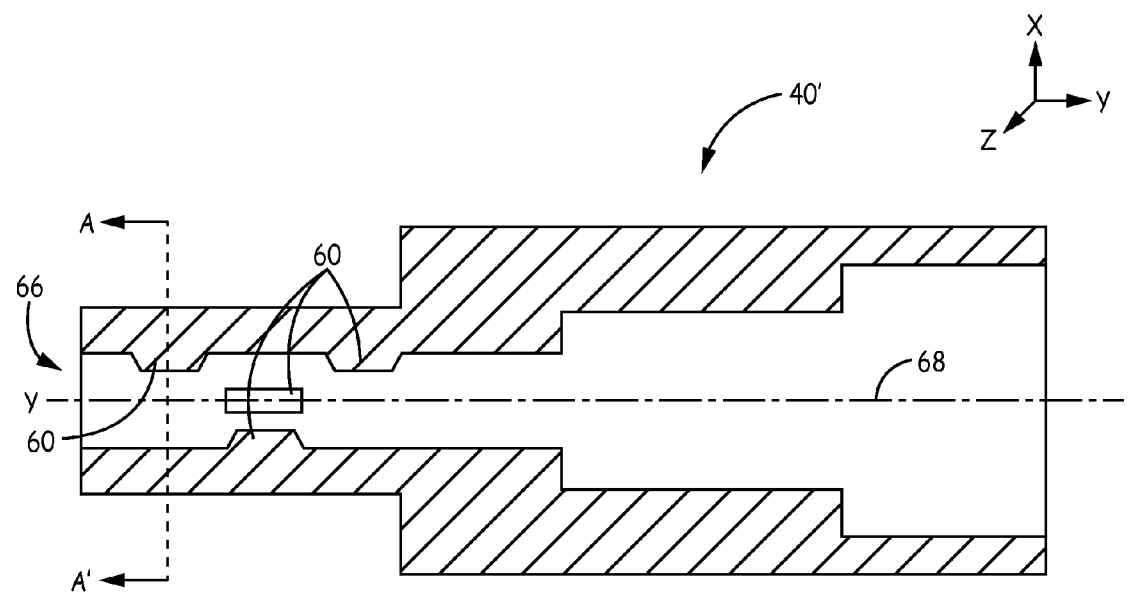
FIGS. 5A-5C illustrate another example of an energy dissipating structure.
Figure 5B:
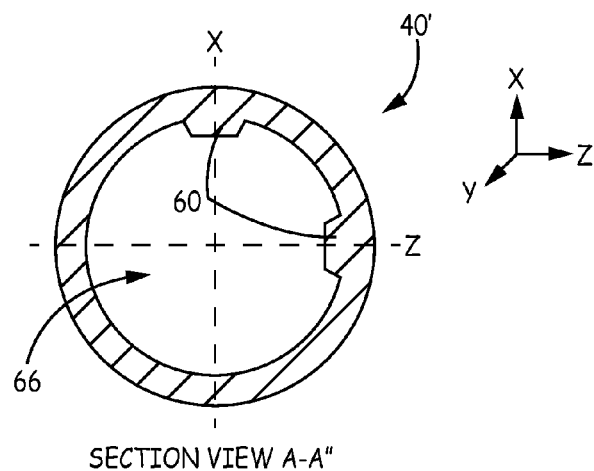
Figure 5C:
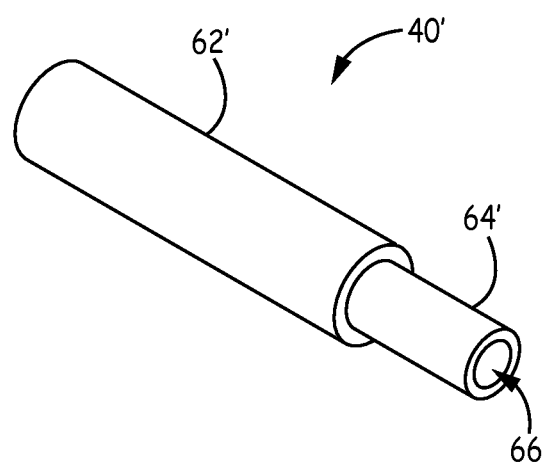

FIGS. 5A-5C illustrate another example of an energy dissipating structure 40' having protrusions 60' of a different shape. Energy dissipating structure 40' of FIGS. 5A-5C conforms substantially to energy dissipating structure 40 of FIGS. 4A-4C except protrusions 60' have a different shape. Energy dissipating structure 40' may, for example, replace energy dissipating structure 40 in the example lead configuration of FIG. 3.

In the example illustrated in FIGS. 5A-5C, protrusions 60' are elongated trapezoidal shaped. Such a shape provides a larger surface area that contact with the filars of coiled conductor 52 than the hemispherical bumps of FIGS. 3 and 4. The elongated trapezoidal shaped protrusions of energy dissipating structure 40' may have a longitudinal length formed to come into contact with multiple filars of coiled conductor 52. This, in effect, provides increased contact points at each interface between energy dissipating structure 40 and coiled conductor 52 since each of the filars of coiled conductor 50 is independent. The elongated trapezoidal shape may also have an arc-shaped innermost surface as the trapezoidal shape extends partially around a portion of the circumference of the energy dissipating structure 40'. Additionally, the elongated trapezoidal shape may have a reduced likelihood of protrusions 60 pushing, extending or otherwise dropping between filars of coiled conductor 52 or between the windings of coiled conductor 52 (e.g., within the space associated with the pitch of the windings of coiled conductor 52). The depth and spacing of protrusions 60 of FIGS. 5A and 5B may be similar to that described above with respect to FIG. 4.

FIG. 5C illustrates an angled view of energy dissipating structure 40'. Energy dissipating structure 40' has at least two sections that having different outer diameters, but unlike energy dissipating structure 40 of FIG. 4C, both the first and second sections have a generally cylindrical shape.

Figure 6:
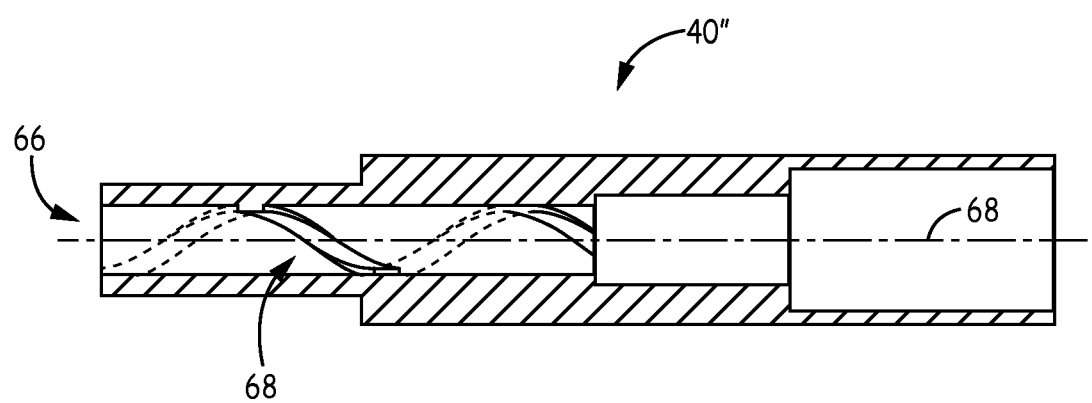
FIG. 6 is a schematic diagram illustrating another example energy dissipating structure.

FIG. 6 is a schematic diagram illustrating another example energy dissipating structure 40" that may be used within a distal end of a lead, such as lead 24 of FIG. 3, in place of energy dissipating structure 40. Energy dissipating structure 40" includes a protrusion that forms an interference thread 68 (also referred to herein as a helical sweep 68). In one example, interference thread or helical sweep 68 may be an integral part of energy dissipating structure 40", e.g., formed via machining of inner surface of energy dissipating structure 40" to form interference thread or helical sweep 68, molding energy dissipating structure 40" to include interference thread or helical sweep 68, rolling the pattern of interference thread or helical sweep 68 into the tubular wall of energy dissipating structure 40", or other technique. In another example, interference thread or helical sweep 68 may be formed by introducing a separate component inserted into the lumen defined by energy dissipating structure 40". The separate component may be an elongated flat wire coil, a helical thread insert, or the like. The separate component may be made from the same material as energy dissipating structure 40" or a different material than energy dissipating structure 40"

In either case, interference thread or helical sweep 68 interferes with coiled conductor 52 to alter the path of coiled conductor 52 resulting in an interference contact with coiled conductor 52 and energy dissipating structure 40". Interference thread or helical sweep 68 may be designed with a different pitch compared to a pitch of coiled conductor 52. For example, interference thread or helical sweep 68 may have an elongated pitch compared to the pitch of coiled conductor 52. Interference thread or helical sweep 68 may also be arranged in the opposite direction as the windings of coiled conductor 52. Having interference thread or helical sweep 68 have a different pitch than and/or opposite direction of the windings of coiled conductor 52 provides an interference contact with coiled conductor 52 that slightly forces coiled conductor 62 off center relative to the central axis. In other words, interference thread or helical sweep 68 pushes a portion of the coil off center relative to the central axis such that coiled conductor follows a slightly undulated, sinusoidal, or helical sweep path through the portion of energy dissipating structure 40 having the interference thread or helical sweep 68. This provides a continuous, constant electrical connection between energy dissipating structure 40 and coiled conductor 52.

The pitch, direction, thickness, depth or other aspect of interference thread or helical sweep 68 may be designed to provide adequate contact with coiled conductor 52 without significantly affecting the extension and retraction capability of coiled conductor 52. For example, pitch and direction of interference thread or helical sweep 68 may be formed to prevent interference thread or helical sweep 68 from extending or otherwise falling between filars or between windings of coiled conductor 52, which may interfere with extension and retraction, particularly when the direction of interference thread or helical sweep 68 is opposite that of coiled conductor 52. In one example, the pitch of interference thread or helical sweep 68 may be at least four times the pitch of coiled conductor 52. In this manner, coiled conductor 52 has traveled at least one and one-half turns before any portions of helical sweep 68 contact coiled conductor 52 on substantially opposite sides of coiled conductor 52. In other words, coiled conductor 52 has traveled at least one and one-half turns before any portions of helical sweep 68 contact coiled conductor 52 at a location approximately 180 degrees from any previous contact point of coiled conductor 52 and helical sweep 68.

In some instances, interference thread or helical sweep 68 (or arrangement of other protrusions 60 such as those in FIGS. 4 and 5) may wrap in the same direction as windings of coiled conductor 52 and may also have essentially the same pitch as windings of coiled conductor 52. In this manner, interference thread or helical sweep 68 (or other protrusions 60) may function as a tooth or guide that actually aids in the extension/retraction of tip electrode 36.

In another example, the effect of helical sweep 68 on coiled conductor 52 may be achieved by using a series of protrusions 60, e.g., bumps, elongated trapezoids or other shaped protrusions, which are located along a path similar to helical sweep 68. In other words, the protrusions are spaced along the longitudinal length and around the circumference of energy dissipating structure 40 to achieve a similar effect of helical sweep 68.

Additionally, the energy dissipating structure illustrated in FIG. 6 may include the one or more kerfs, grooves, or notches to allow that region of energy dissipating structure 40 to bend or flex slightly allowing for more intimate contact when the lead moves, as described above with respect to FIG. 4.

Figure 7A:
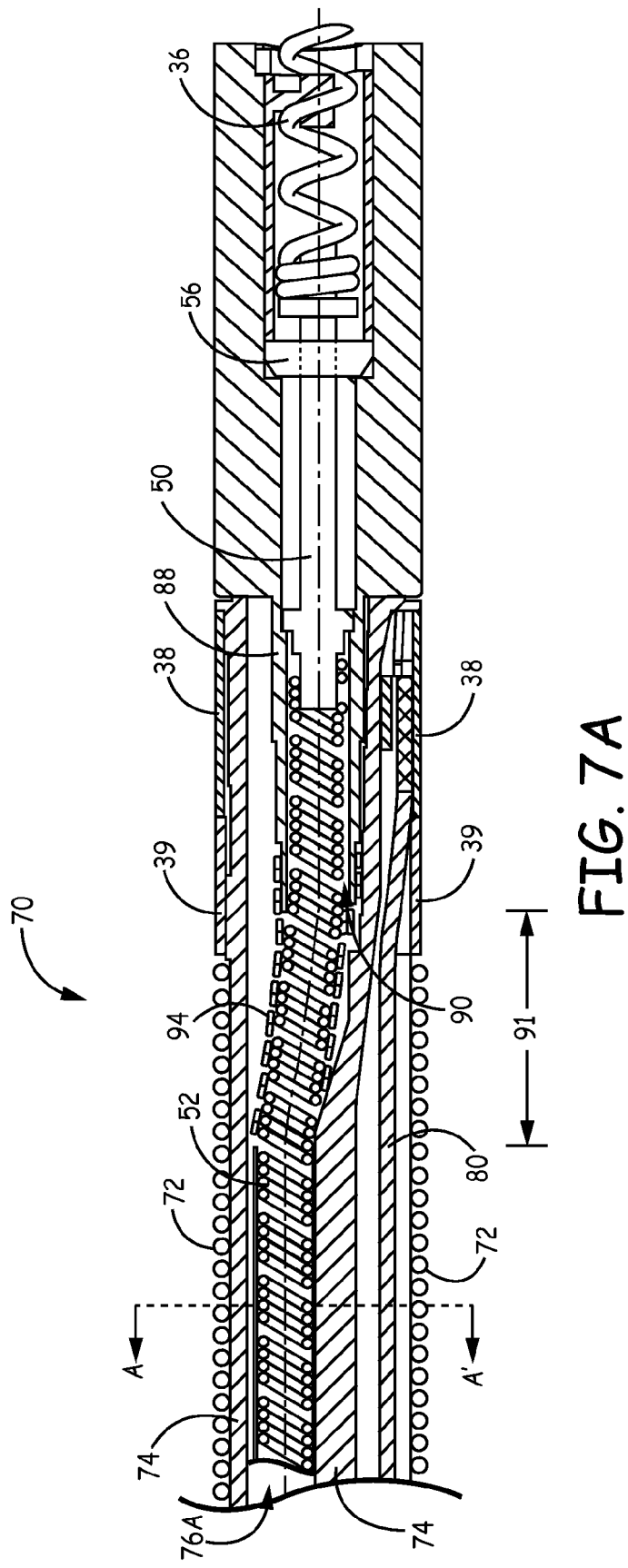
FIGS. 7A and 7B are schematic diagrams illustrating various views of a distal end of another example lead.
Figure 7B:
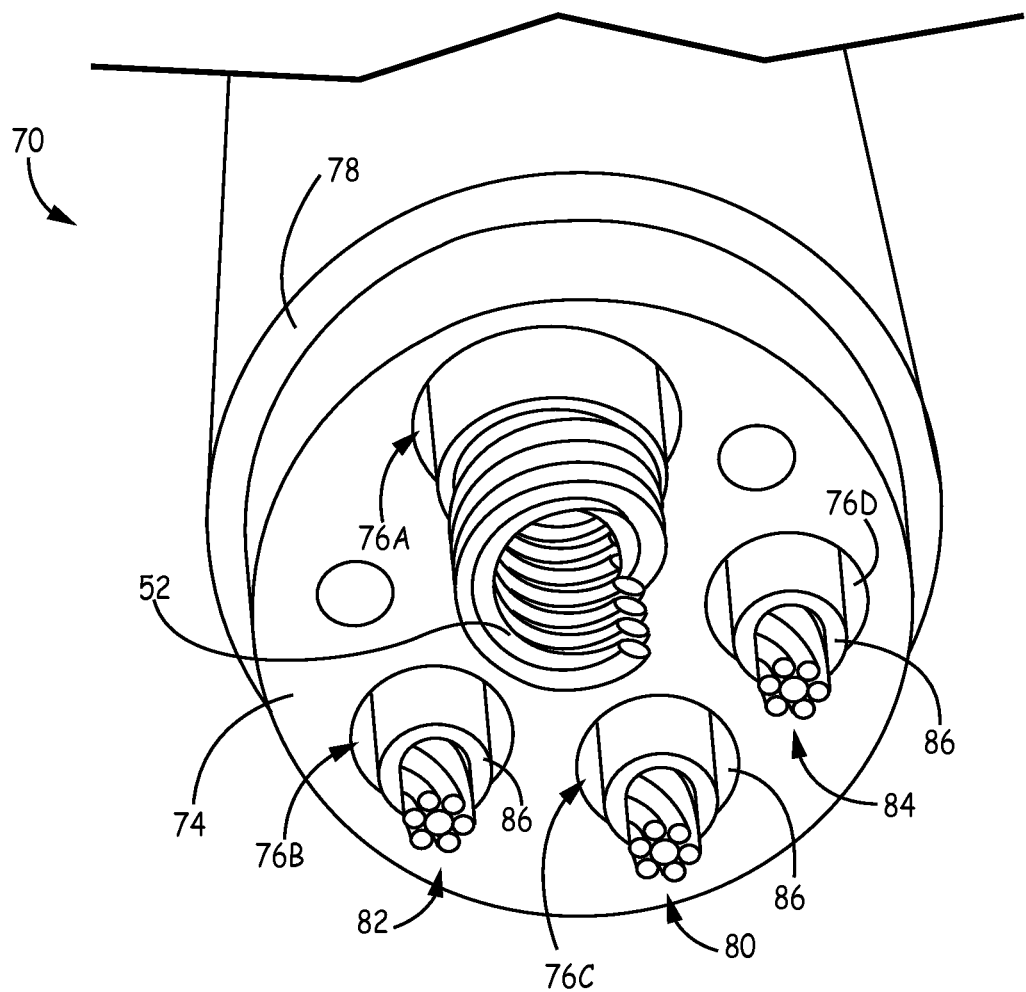

FIGS. 7A and 7B are schematic diagrams illustrating various views of a distal end of another example lead 70. Lead 70 may correspond with lead 24a or lead 24b of FIG. 2. Lead 70 includes a tip electrode 36, ring electrode 38, and a defibrillation electrode(s) 72. Each of tip electrode 36, ring electrode 38, and defibrillation electrode 72 is electrically coupled to one or more electronic components on PCB 30 of IMD 22. As such, separate electrical paths exist from a proximal end of lead 70 (which is coupled to connector block 42 of IMD 22) to respective ones of tip electrode 36, ring electrode 38, and defibrillation electrode 72.

FIG. 7A illustrates a longitudinal cross-sectional view of the distal end of lead 70 and FIG. 7B illustrates a section view of the distal end of lead 70 from A-A'. As illustrated in FIG. 7B, lead 70 includes multi-lumen lead body 74, which includes four lumens 76A-76D through which each of the four conductors of lead 70 extend. Lead body 74 is typically comprised of extruded silicone rubber or other non-conductive, biocompatible material. Lead body 74 may be covered by sheathing 78 that protects the components of lead 70 from the environment of the body in which it is implanted. Sheathing 78 may be comprised of a polyurethane or other non-conductive, bio-compatible material.

Conductors 80, 82 and 84 are illustrated in FIG. 7B as being stranded cable conductors in which a plurality of wire filars are wrapped around central wire filar inside sheathing 86. Conductors 80, 82, and 84 are connected to respective electrodes. In the example of FIG. 7B, conductor 80 is connected to ring electrode 38 (as illustrated in FIG. 7A). Although not illustrated in FIG. 7, conductors 82 and 84 are connected to respective defibrillation electrodes 72. Conductor 80 is connected to ring electrode 38. Although illustrated as stranded cable conductors, one or more of conductors 80, 82, and 84 may be other types of conductors, such as modified stranded cable conductors (e.g., having a non-conductive core), coiled conductors, or the like.

The electrical path from the proximal end of lead 70 to tip electrode 36 includes a coiled conductor 52 and an electrode shaft 50 similar to lead 24 illustrated in FIG. 3. Electrode shaft 50 is connected at one end to coiled conductor 52 and at the other end to tip electrode 36. Coiled conductor 52, electrode shaft 50 and tip electrode 36 may all be formed at least partially from a conductive material, such as titanium, titanium alloy, tantalum, tantalum alloy, platinum, platinum iridium, conductive polymers, and/or other suitably conductive material or combination of materials. Coiled conductor 52, electrode shaft 50 and tip electrode 36 may be all formed of the same conductive material or different conductive materials. In one example, coiled conductor 52 is a multi-filar coil having a plurality of co-radially wound bare wire filars within a sheathing 86.

The mechanical coupling of coiled conductor 52, electrode shaft 50 and tip electrode 36 provides a mechanical relationship that may, in some instances, allow for mechanical control of tip electrode 36 such that it may be extended from and retracted within the distal end of lead 70. During implantation, for example, a physician or other user may interact with lead 70 to rotate coiled conductor 52, which causes electrode shaft 50 to rotate and extend tip electrode 36 from the distal end of lead 70. In this manner, tip electrode 36 may be screwed into the target tissue location. As such, coiled conductor 52 may have sufficient rigidity to assist in attaching tip electrode 36 to the target tissue location while being flexible enough to navigate through body lumens, e.g., through one or more veins. In other examples, tip electrode 36 may be extended via a translational force instead of a rotational force. In other instances, electrode shaft 50 may be formed to receive a stylet to guide lead 70 during implantation or to allow a user to extend and/or retract tip electrode 36. In further instances, lead 70 may not include an electrode shaft 50. Instead, conductor 52 may be directly connected to tip electrode 36 and may or may not allow for mechanical control of tip electrode 36.

Lead 70 includes an energy dissipating structure 88 that is electrically coupled near the distal end of lead 70 to the electrical path from the proximal end of lead 70 to tip electrode 36. Energy dissipating structure 88 is electrically coupled to coiled conductor 52 throughout at least a portion of transition section 91 to provide a second electrical path through energy dissipating structure 88 that is in parallel with the electrical path through tip electrode 36.

Energy dissipating structure 88 presents a high impedance at low frequencies, such as those frequencies used for pacing or other stimulation therapies (e.g., ~1 kHz for pacing signals). As such, only a small amount of current is redirected away from tip electrode 36, e.g., along the second electrical path to energy dissipating structure 88, at low frequencies. In this manner, energy dissipating structure 88 functions by essentially having electrical isolation at low pacing frequencies allowing pacing to occur at the tip electrode surface.

Energy dissipating structure 88 presents a low impedance at high frequencies, such as those frequencies produced by MRI device 16 (greater than 1.0 MHz), resulting in a significant amount of the induced current being redirected away from the first electrical path through tip electrode 36 to the second electrical path through energy dissipating structure 88. Thus, energy dissipating structure 88 functions by coupling a significant amount of the higher frequency energy through the energy dissipating structure 88. In one example, an electrical lead with an energy dissipating structure 88 as described herein may result in at least 50% of the energy induced by high frequency RF signals of an MRI device to be redirected away from tip electrode 36 while less than 10% of the energy associated with a pacing therapy is directed through energy dissipating structure 40.

In some instances, energy dissipating structure 88 has a surface area that is significantly larger than a surface area of tip electrode 36. The surface area of energy dissipating structure 88 may, in one example, be between approximately 20-100 mm$^2$, which is at least approximately ten times larger than the surface area of tip electrode 36. A large surface area ratio, defined by the ratio of the surface area of energy dissipating structure 88 to the surface area of tip electrode 36 is desired to dissipate the induced current over a larger area to reduce heating at any specific location.

Energy dissipating structure 88 may include a conductive material that is at least partially covered by a layer of insulating material. In one example, the insulation material may cover at least the portion of energy dissipating structure 88 that is exposed to the bodily fluid and/or tissue of patient 12 such that the outer surface of the conductive material of energy dissipating structure 40 does not contact a body of the patient when implanted. In other instances, however, conductive material of energy dissipating structure 88 may be directly exposed to bodily fluid and/or tissue, i.e., not include the layer of insulating material. The conductive material may be an electrically and thermally conductive material, such as titanium, titanium alloy, tantalum, tantalum alloy, platinum, platinum iridium, conductive polymers, and/or other suitably conductive material or combination of materials.

The insulating material may cover an outer surface of conductive material or at least a portion of the outer surface of conductive material. Insulating material may affect the impedance of energy dissipating structure 88 and reduce the effect of energy dissipating structure 88 on the tip electrode to tissue interface impedances. As the thickness of insulating material increases, the capacitance associated with energy dissipating structure 88 decreases and the impedance of energy dissipating structure 88 increases. As a result the amount of current redirected to energy dissipating structure 88 is reduced, but there is less interference with therapy delivered by IMD 22. As the thickness of insulating material 64 decreases, the capacitance associated with energy dissipating structure 88 increases and the impedance of energy dissipating structure 88 decreases. As a result the amount of current (even at low frequencies) redirected to energy dissipating structure 88 is increased, which may affect therapy delivered IMD 22.

For example, an energy dissipating structure 88 having a surface area of approximately 22 square millimeters (mm$^2$) and an insulating material having a dielectric constant of approximately 4.0, an insulating material thickness of approximately 68 micrometers provides an impedance of approximately 10 Ohms and a capacitance of approximately 250 pF, a thickness of approximately 34 micrometers provides an impedance of approximately 5 Ohms and a capacitance of approximately 500 pF, and a thickness of approximately 17 micrometers provides an impedance of approximately 2.5 Ohms and a capacitance of approximately 1 nF. These values are only exemplary in nature. The electrical characteristics of energy dissipating structure 88 may take on different values depending on the construction of the distal end of lead 70, e.g., based on the surface area of tip electrode 36, the surface area of energy dissipating structure 88, the thickness of insulating material, the material from which the various components are constructed, and the like.

The thickness of insulating material may be selected by a therapy system designer to achieve a satisfactory tradeoff between capacitance and impedance. Numerous techniques may be employed to introduce insulating material over the outside of energy dissipating structure 88 and/or partially inside energy dissipating structure 88. Exemplary techniques include chemical vapor deposition, dip layer, spraying, thermal reflow, or thermal extrusion or molding.

Insulating material may also cover at least a portion of an inner surface of conductive material. Insulating material on the inner surface may prevent conductive material of energy dissipating structure 88 from making direct contact with the conductive material of tip electrode 36, electrode shaft 50 and/or coiled conductor 52 at locations other than desired. In some instances, the insulating material may even cover the surface of the portion of conductive material contacting coiled conductor 52. In this case, the coupling between energy dissipating structure 40 and coiled conductor 52 is a non-conductive (e.g., capacitive or thermal) coupling instead of a conductive coupling. In some instances, energy dissipating structure 88 may include more than one layer of insulating material, with each layer being made of the same or different insulating material. Insulating material may include parylene, metal oxides, polyimide, urethane, silicone, tetrafluroethylene (ETFE), polytetrafluroethylene (PTFE), polyether ether ketone (PEEK), oxides, or other suitable non-conductive material or combination of materials.

It is desirable that the contact between energy dissipating structure 40 and coiled conductor 52 is continuous, as intermittent metal-metal contact of coiled conductor 52 and energy dissipating structure 40 may generate electrical noise. Moreover, with extendable\retractable leads this electrical connection/contact, the tip electrode 36 (which may be a helix as illustrated in FIG. 3) and inner circuit (which may include coiled conductor 52 and electrode shaft 50) may rotate while the energy dissipating structure 40 remains fixed. It is thus desirable to have an electrical connection/contact that reduces the effect on lead extension performance while maintaining constant contact and presents a low resistance connection during MRI procedures. It may also be desirable to have the connection/contact mitigate electrical noise that could be generated via by intermittent metal-metal contact of inner circuit and energy dissipating structure 40 or by this electrical connection. Noise generated by intermittent contact could present itself as cardiac signals since the lead tip is moving at the same rate as the heart in some cardiac implementations. To help mitigate this noise potential the energy dissipating structure 40 can be completely isolated with the exception of this electrical connection and/or this electrical connection need to be of low enough resistance to drain off/ground the metal components resting potential such that noise is minimized by metal to metal contact.

Past solutions have been to make springs, spring clips, conductive seals, or the like that will make these electrical connections. These options require that separate component (s) be added that makes contact with electrode shaft 50. Some of these solutions may utilize components that are constructed of a material that is harder than that of electrode shaft 50 (which may be constructed of materials such as platinum/ iridium (Pt/Ir)) so that the electrical connection component will not easily plastically deform during assembly and use. The softer material of electrode shaft 50 may, in some instances, be subject to galling when used in combination with harder spring materials. Additionally, the smaller sizes and tolerances of the springs, spring clips, conductive seals, or the like, make these components difficult and/or expensive to manufacture.

In accordance with the techniques of this disclosure, lead 70 is formed to make electrical connection between coiled conductor 52 and the energy dissipating structure 88 by way of an interference contact. Energy dissipating structure 88 defines a lumen 90. Lumen 90 is offset relative to lumen 76A. For example, lumen 90 and lumen 76A may lie in different longitudinal planes. In other words, a central axis of lumen 76A is offset relative to a central axis of lumen 90. In the example of FIGS. 7A and 7B, lumen 76A is offset toward an edge of lead body 74, whereas lumen 90 corresponds with a center of lead body 74, e.g., coiled conductor 52 transitions from an asymmetric lumen to center lumen. However, lumens 76A and 90 may both be offset relative toward the edge of lead body 74, lumen 76A may correspond to a center of lead body 74 and lumen 90 may be offset toward an edge of lead body 74, or the like. The configuration illustrated in FIGS. 7A and 7B is for illustration purposes only and should not be considered limiting of the design.

In the example of FIG. 7A, coiled conductor 52 transitions from lumen 76A defined by the lead body 74 to a lumen 90 defined by energy dissipating structure 88. This transition from lumen 76A of lead body 74 to lumen 90 defined by energy dissipating structure 88 causes coiled conductor 52 to bend throughout at least a portion of transition section 91. In this manner, conductor 52 is forced off center via a lumen position change within lead body 74. Because coiled conductor 52 has many properties of a spring, when coiled conductor 52 is shifted out of plane throughout transition section 91, the natural response of coiled conductor 52 is to realign along a relatively straight central axis. As such, coiled conductor 52 produces forces throughout at least a portion of transition section 91 in an attempt to realign the proximal and distal ends of the transitioned section of coil 52. For example, coiled conductor 52 may exhibit forces at the proximal and distal ends of transition section 91 to provide a relatively continuous interference contact near the proximal and distal ends of transition section 91. These forces may be utilized to provide a substantially continuous electrical contact with energy dissipating structure 88.

In the example illustrated in FIG. 7A, a wire may be wound to form a secondary outer coil 94 that extends around the coiled conductor 52 to make contact with coiled conductor 52 throughout at least a portion of transition section 91. Secondary outer coil 94 may be mechanically coupled to energy dissipating structure 88, e.g., via crimping, welding, or the like. The end of secondary outer coil 94 opposite the connection to energy dissipating structure 88 may not be connected mechanically to anything. The free floating end of secondary outer coil 94 proximate to the lumen 76A may also have spring properties similar to those discussed above with respect to coiled conductor 52 and thus provide forces to aid in the interference contact at portions of transition section 91. In other instances, secondary coil 94 formed by the wire may provide sufficient spring force to mechanically and electrically couple to energy dissipating structure 88 without any crimping, welding, or the like.

In some instances, secondary outer coil 94 may be formed to have an inner diameter that is approximately equal to or possibly slightly smaller than the outer diameter of coiled conductor 52 when secondary outer coil 94 is in its relaxed state. During assembly, secondary outer coil 94 may, in some instances, be pushed together, thus slightly expanding the diameter of the secondary coil 94. Coiled conductor 52 may be strung through the pushed together the secondary outer coil 94 and then the secondary outer coil 94 may be released to its relaxed state. When the secondary outer coil 94 is released to its relaxed state secondary outer coil 94 may contact coiled conductor 52 throughout the entire portion or at least a large portion of the transition section 91, thus providing the interference contact.

Utilizing secondary outer coil 94 to provide the interference connection with energy dissipating structure 88 may enable movement and/or flexing throughout the transition section 91 to minimize bending during extension and retraction, and to allow a stylet to be moved in and out of this section more easily. The remainder of energy dissipating structure 88 may not be flexible.

In any case, the frictional force and contact between coiled conductor 52 and secondary outer coil 94 provides an electrical connection achieved by the friction between the coiled conductor 52 and secondary outer coil 94. In this manner, the interference contact is accomplished using the inherent spring properties of coiled conductor 52 and secondary outer coil 94.

In some instances, the coupling between energy dissipating structure 88 and coiled conductor 52 throughout the transition section 91 may be via a non-conductive coupling, e.g., capacitive coupling or thermal coupling, to tip electrode 36 instead of an electrical (e.g., metal to metal) coupling. For example coiled conductor 52 and/or secondary outer coil 94 may be insulated throughout the transition portion, but still allow high frequency RF energy to couple from coiled conductor 52 through secondary outer coil 94 to energy dissipating structure 88.

The wire used to form secondary outer coil 94 may be a single filar or multi-filar wire and may be round wire, flat wire, or other shaped wire. The wire used to form secondary outer coil 94 in the illustrated example is a dual-filar flat wire. In other examples, components other than secondary outer coil 94 may provide the interference contact along the transition segment 91, such as a wire mesh or other component.

Figure 8:
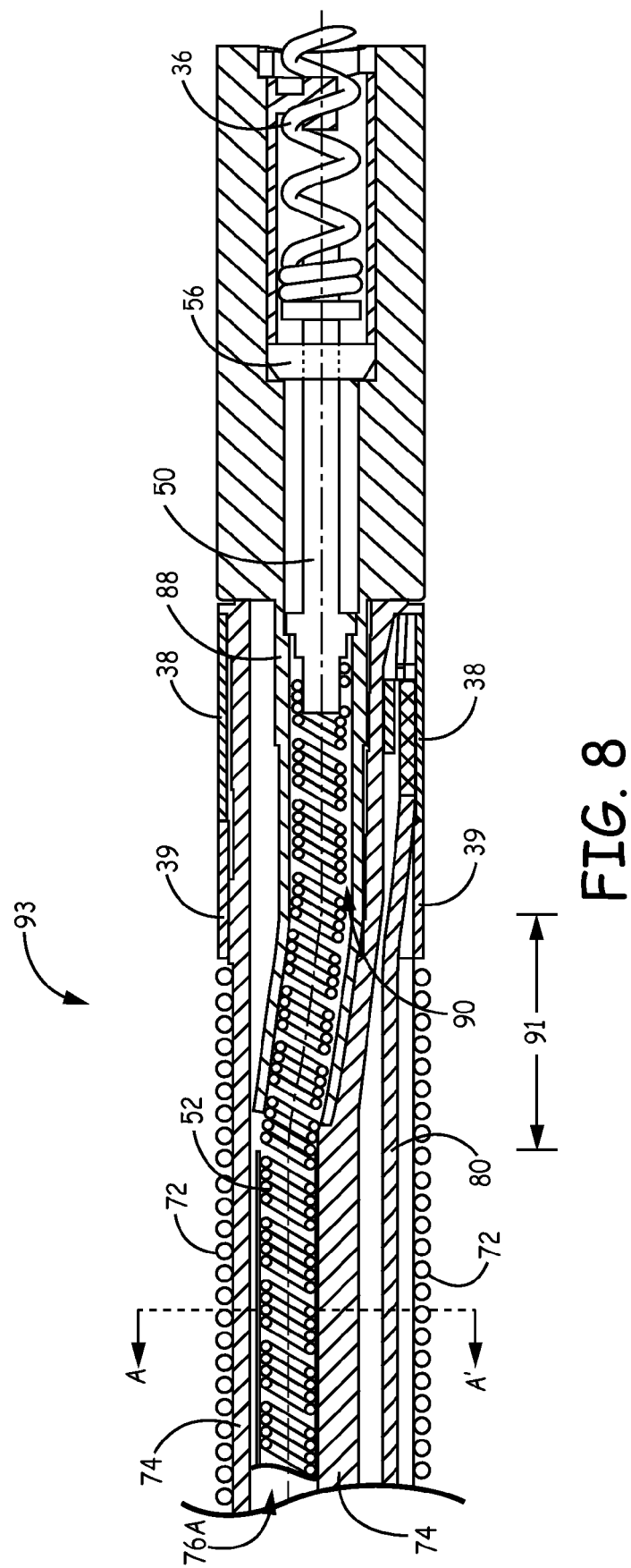
FIG. 8 illustrates another example of a distal end of another example lead.

FIG. 8 is a schematic diagram illustrating a view of a distal end of another example lead 93. The distal end of lead 93 substantially conforms to the distal end of lead 70 of FIG. 7, but energy dissipating structure 88 is an integral piece formed to provide the interference contact along at least a portion of transition section 91. In other words, the proximal end of energy dissipating structure 88 is formed, e.g., via bending, machining, or other technique, into a shape similar to transition segment 91 instead of utilizing a separate, secondary outer coil 94 as described with respect to FIG. 7A. In this manner, the interference contact is accomplished using the inherent spring properties of coiled conductor 52 creating contact with the portion of energy dissipating structure 88 extending along transition segment 91.

The portion of energy dissipating structure 88 formed to provide the interference contact may, in some instance, be formed to allow for movement and/or flexing throughout the transition section 91 to minimize bending during extension and retraction, and to allow a stylet to be moved in and out of this section more easily. For example, the portion of energy dissipating structure 88 formed to provide the interference contact may be formed relatively thin to provide the desired flexing while the remainder of energy dissipating portion 88 does not provide much flex. In another example, the portion of energy dissipating structure 88 formed to provide the interference contact may include the one or more kerfs, grooves, or notches to allow that region of energy dissipating structure 40 to bend or flex slightly allowing for more intimate contact when the lead moves, as described above with respect to FIG. 4.

In some instances, the coupling between energy dissipating structure 88 and coiled conductor 52 throughout the transition section 91 may be via a non-conductive coupling, e.g., capacitive coupling or thermal coupling, to tip electrode 36 instead of an electrical (e.g., metal to metal) coupling. For example coiled conductor 52 and/or the portion of energy dissipating structure 88 extending along transition segment 9 lmay be insulated, but still allow high frequency RF energy to couple from coiled conductor 52 to energy dissipating structure 88.

Figure 9:
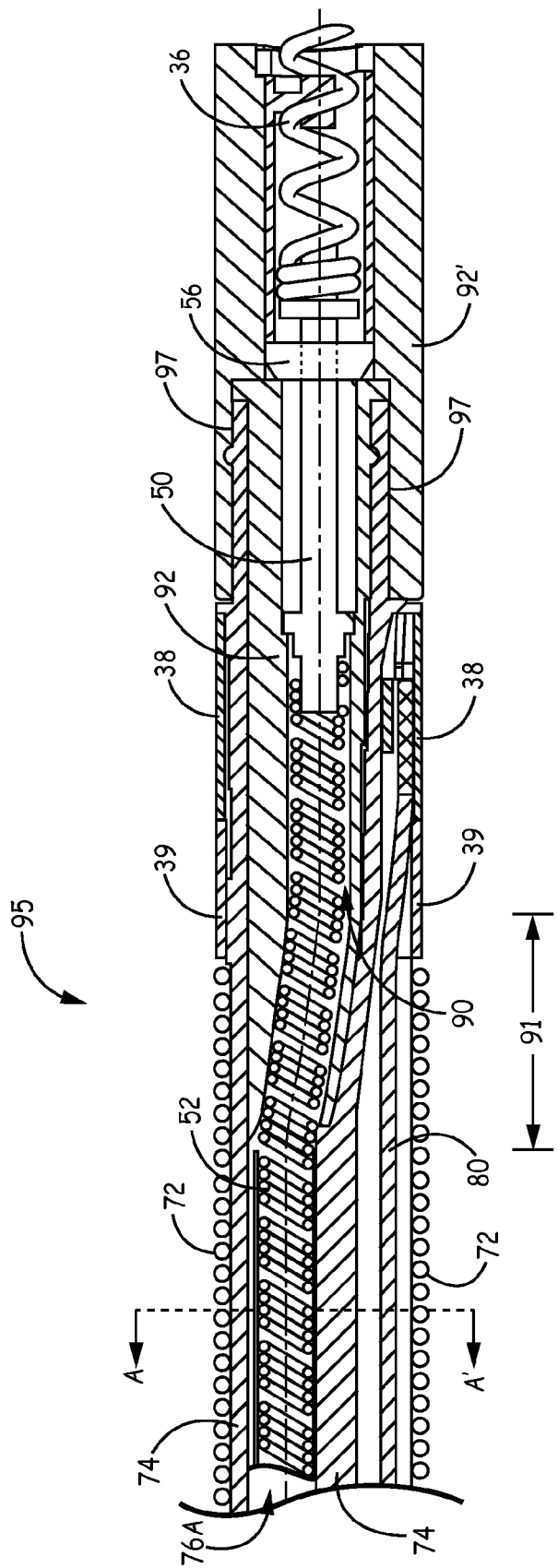
FIG. 9 illustrates another example of a distal end of another example lead.

FIG. 9 is a schematic diagram illustrating a view of a distal end of another example lead 95. The distal end of lead 95 substantially conforms to the distal end of lead 93 of FIG. 8, but energy dissipating structure 88 is composed of two separate portions that may provide easier assembly and/or manufacturability. As illustrated in FIG. 9, a first portion 92 of energy dissipating structure 88 is formed from transition section 91 toward the distal end of the lead and end near where seal 56 of the assembled lead will be located. First portion 92 of energy dissipating structure may be formed via any of a number of techniques including molding.

Second portion 92' of energy dissipating structure 88 if formed separately from first portion 92. Second portion 92' may be formed with an indent arranged to receive a notch of insulation portion of the lead body at location 97. In other instances, the insulation portion may be formed with an indent to receive a notch of second portion 92'. In either case, when second portion 92' of energy dissipating structure 88 is put into place, first portion 92 and second portion 92" are in good physical and electrical contact to form energy dissipating shunt 88. First portion 92 and second portion 92' may be constructed of the same or different electrically and/or thermally conductive material.

Although FIGS. 7, 8, and 9 are described in the context of a lead that include a conductive electrode shaft that is coupled at a proximal end to coiled conductor and coupled at a distal end to the tip electrode, these lead configuration may not include a conductive electrode shaft, but instead may have the coiled conductor directly connected to the tip electrode.

Figure 10:
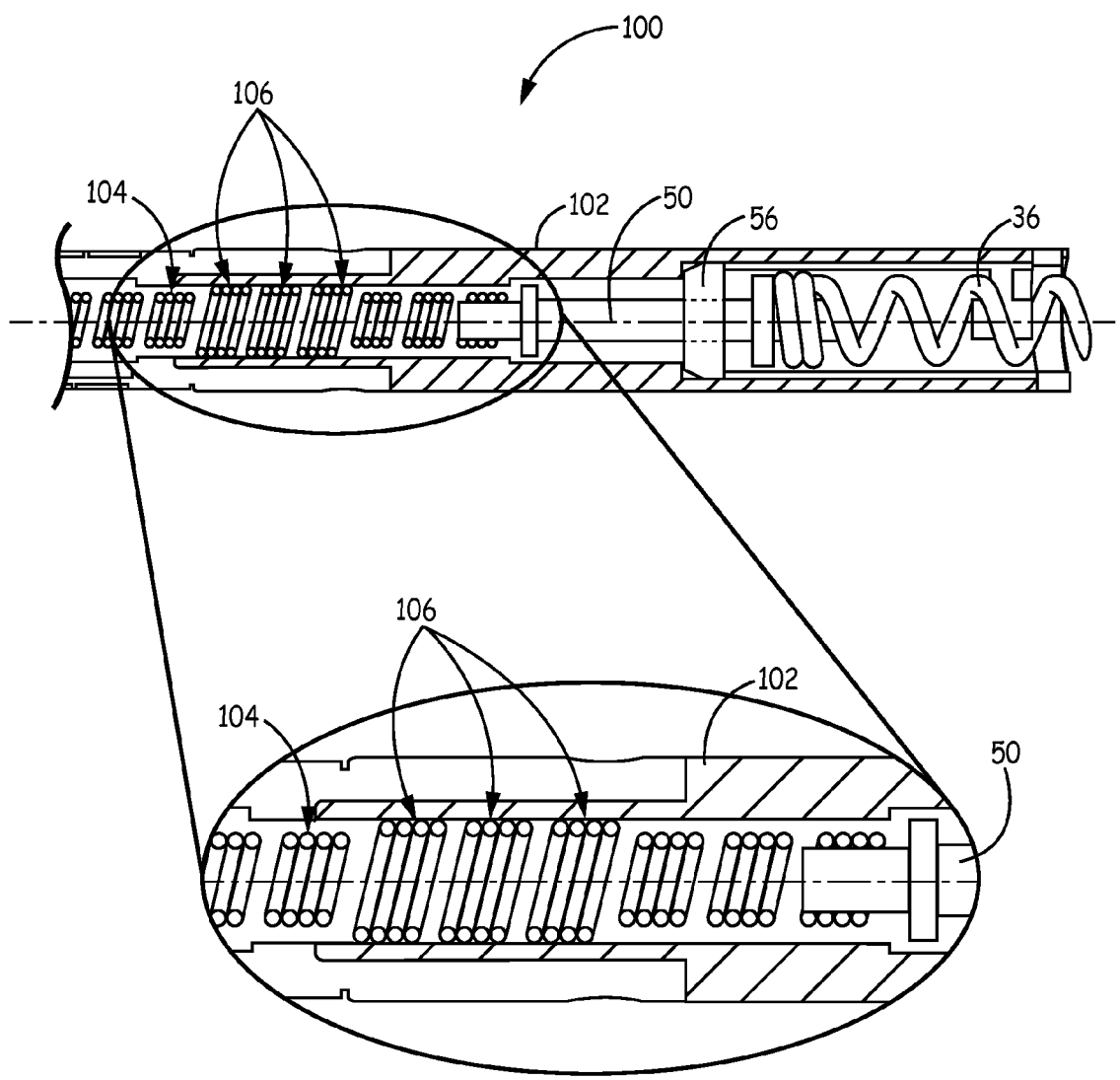
FIG. 10 illustrates another example of a distal end of another example lead.

FIG. 10 illustrates another example of a distal end of a lead 100, such as one or both of leads 24a or lead 24b of FIG. 2. Lead 100 includes a tip electrode 36 that is part of an electrical path from a proximal end of lead 100 that includes coiled conductor 104 and electrode shaft 50. Lead 100 is similar to lead 24 of FIG. 3 except energy dissipating shunt 102 does not include protrusions designed to provide an interference contact with coiled conductor 104. Instead, the portion of coiled conductor 104 extending through the lumen formed by energy dissipating structure 102 is designed to provide an interference contact with energy dissipating structure 102.

In the example illustrated in FIG. 10, coiled conductor 104 is formed to have a larger outer diameter for a specific distance to create at interference contact sections 106. In other words, coiled conductor 104 includes sections 106 that have a larger outer diameter than the remaining portions of coiled conductor 104. These sections 106 have an outer diameter that is approximately equal to and possibly slightly larger than the inner diameter of energy dissipating structure 102 such that an interference contact is made between these sections 106 of coiled conductor 104 and energy dissipating structure 102.

Sections 106 have inherent spring-like properties that are used to generate/make the interference contact between the stationary energy dissipating structure 102 and sections 106 of coiled conductor 104. In particular, the spring-like properties of sections 106 exert an outward force (e.g., away from a central axis of coiled conductor 104) that provides a constant contact between coiled conductor 104 and energy dissipating structure 102. In instances in which lead 100 is an active fixation lead that is capable of extension and retraction, sections 106 are designed to provide enough force to maintain continuous contact with energy dissipating structure, but not impede the extension/retraction capabilities of the lead during implantation. Sections 106 of coiled conductor 104 may, in some instances, be formed during winding. In other instances, sections 106 of coiled conductor 104 may be formed post winding, e.g., during construction of the distal end of lead 100.

In the example illustrated in FIG. 10, each of the four filars of coiled conductor 104 have the larger outer diameter for at least one winding along the longitudinal length of lead 100 to provide the interference contact. In other examples, fewer than all four filars of coiled conductor 104 may have the larger outer diameter. Coiled conductor 104 illustrated in FIG. 10 has the larger outer diameter for a plurality of turns 106 of coiled conductor 104 throughout the proximal portion of energy dissipating structure 102 thus providing the interference contact. In other examples, coiled conductor 104 may have the larger outer diameter for more or fewer turns of coiled conductor 104.

Figure 11:
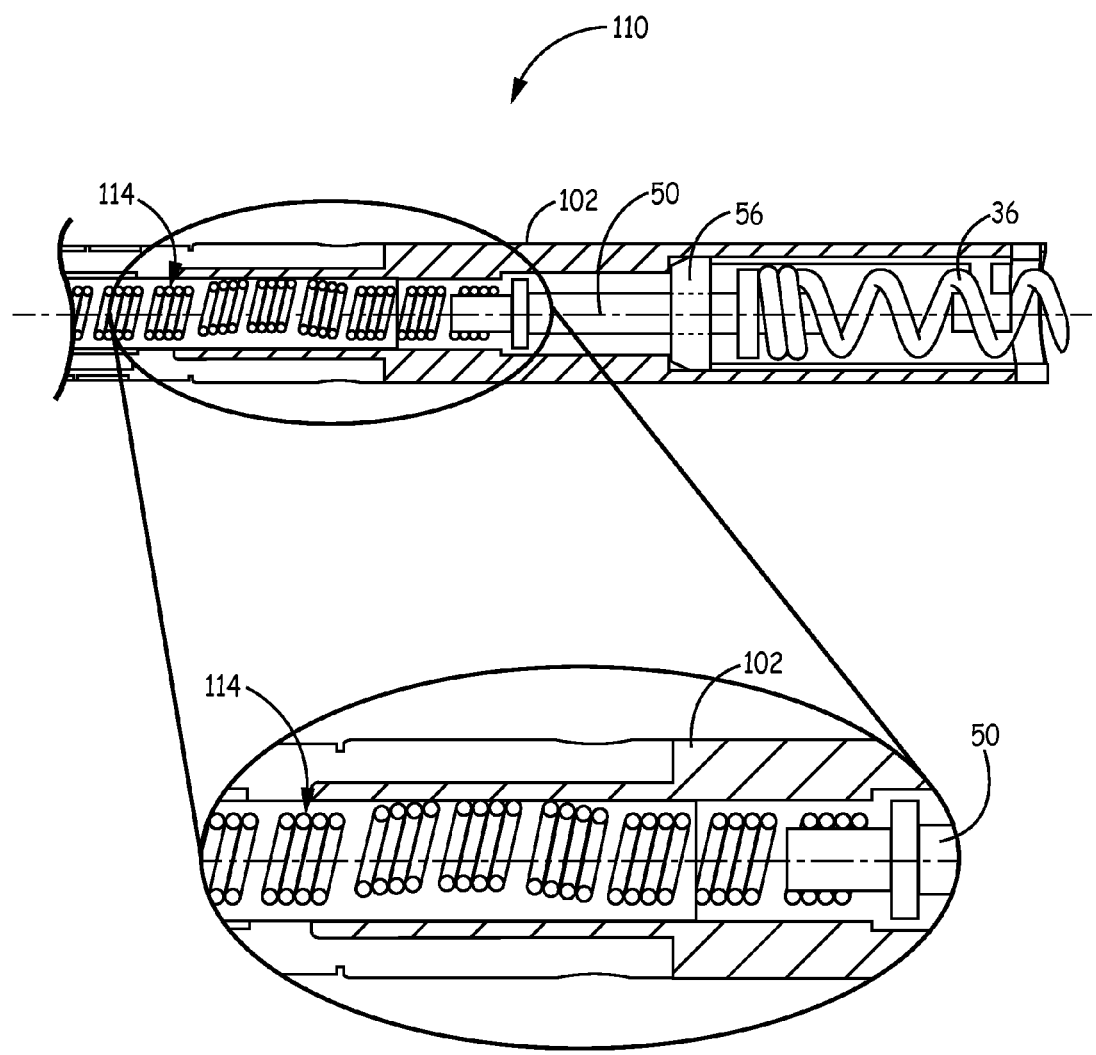
FIG. 11 illustrates another example of a distal end of another example lead.

FIG. 11 illustrates another example of a distal end of a lead 110, such as one or both of leads 24a or lead 24b of FIG. 2. Lead 110 includes a tip electrode 36 that is part of an electrical path from a proximal end of lead 110 that includes coiled conductor 114 and electrode shaft 50. Lead 110 is substantially similar to lead 100 of FIG. 10 except the interference contact between coiled conductor 114 and energy dissipating structure 102 is created by forming at least the portion of coiled conductor 114 extending through the lumen formed by energy dissipating structure 102 with a geometry to provide substantially continuous contact with energy dissipating structure 102.

Coiled conductor 114 is constructed to have a pre-formed shape. Coiled conductor 114 may be pre-formed during winding or after winding, but prior to lead assembly of the distal end of lead 110 into a shape other than a typical straight conductor. For example, coiled conductor 114 may be constructed into a J-shaped conductor and/or formed to include a loop. When the coiled conductor 114 having the pre-formed shape is placed within the lumen defined by energy dissipating structure 102, the spring-like properties of coiled conductor 114 wanting to return to its pre-formed shape results in an interference contact with energy dissipating structure 102. In the example illustrated in FIG. 11, the resulting shape of the portion of coiled conductor 14 through energy dissipating structure 102 is an arc shape. In this manner, the coiled conductor 102 may be pre-formed with a geometry such that a controlled sections come in contact with the energy dissipating structure 102. Depending on the pre-formed shape of coiled conductor 114, the geometry of the portion of coiled conductor 114 extending within energy dissipating structure 102 may have a shifting, sinusoidal, undulated or other geometry.

When assembled into lead 110, the geometry of the portion coiled conductor 114 extending within energy dissipating structure 102 is configured to provide a continuous contact with energy dissipating structure 102 at one or more locations, even during movement of lead 110. In particular, coiled conductor 114 exerts a frictional force that provides a constant contact, but, at least in instances in which lead 110 is an active fixation lead that is capable of extension and retraction, does not impede the extension/retraction capabilities of the lead during implantation.

Figure 12:
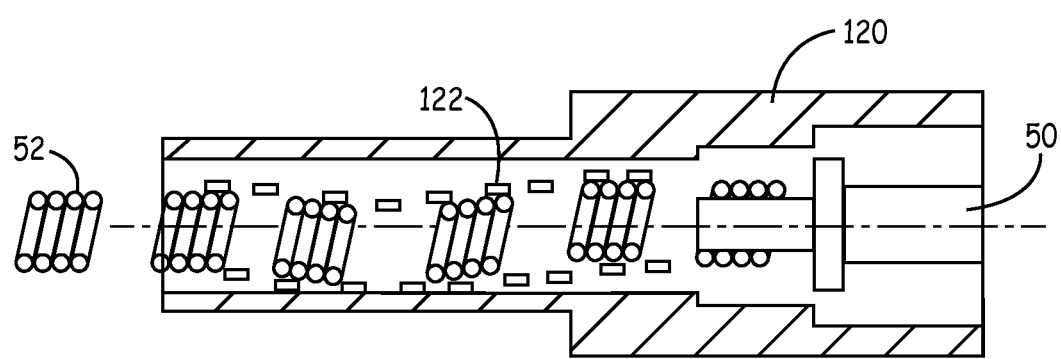
FIG. 12 illustrates another example of a distal end of another example lead.

FIG. 12 is illustrates another example of a distal end of a lead, such as one or both of leads 24a or lead 24b of FIG. 2. This lead is substantially similar to lead 110 of FIG. 11 except a preformed coil 122 is placed within shunt 120 and a conventional, straight coiled conductor 52 is extended through the pre-formed coil 122 to achieve the interference contact.

It is understood that the present disclosure is not limited for use in pacemakers, cardioverters or defibrillators. Other uses of the leads described herein may include uses in patient monitoring devices, or devices that integrate monitoring and stimulation features. In those cases, the leads may include sensors disposed on distal ends of the respective lead for sensing patient conditions. The leads described herein may be used with a neurological device such as a deep-brain stimulation device or a spinal cord stimulation device. In other applications, the leads described herein may provide muscular stimulation therapy, gastric system stimulation, nerve stimulation, lower colon stimulation, drug or beneficial agent dispensing, recording or monitoring, gene therapy, or the like. In short, the leads described herein may find useful applications in a wide variety medical devices that implement leads and circuitry coupled to the leads.

Various examples have been described. Most of the example lead configurations described include a conductive electrode shaft that is coupled at a proximal end to coiled conductor and coupled at a distal end to the tip electrode. All of these example lead configurations, however, may not include a conductive electrode shaft, but instead may have the coiled conductor directly connected to the tip electrode.

Additionally, any of the lead configurations described herein may include a kerf, groove or notch may be formed (e.g., via laser or other mechanism) on energy dissipating to allow that energy dissipating structure to bend or flex slightly allowing for more intimate contact with the coiled conductor when the lead moves. The kerf, groove or notch may be formed as described above with respect to FIG. 4.

These and other embodiments are within the scope of the following claims. Additionally, skilled artisans appreciate that other dimensions may be used for the mechanical and electrical elements described herein. It is also expected that the teachings herein, while described relative to a bipolar lead, can also be applied to a unipolar lead or other multipolar configurations as well as co-radial and multi-lumen configurations. These and other examples are within the scope of the following claims.

The invention claimed is:

1. A medical electrical lead comprising:
   a lead body having a proximal end configured to couple to an implantable medical device and a distal end;
   a conductive electrode shaft located near the distal end within the lead body;
   a coiled conductor extending within the lead body from the proximal end and coupled to a first end of the conductive electrode shaft;
   an electrode located near the distal end of the lead body and coupled to an opposite end of the conductive electrode shaft as the coiled conductor;
   an energy dissipating structure located near the distal end of the lead body and formed from a conductive material that defines a lumen through which a portion of the coiled conductor extends, wherein the portion of the coiled conductor extending through the lumen defined by the energy dissipating structure is formed to provide an interference contact with the energy dissipating structure; and
   a layer of insulating material covering at least an outer surface of the conductive material of the energy dissipating structure such that the outer surface of the conductive material of the energy dissipating structure does not directly contact a body of the patient when implanted.

2. The medical electrical lead of claim 1, wherein the portion of the coiled conductor extending through the lumen defined by the energy dissipating structure is formed to have one or more sections having windings of a first outer diameter and one or more sections having windings of a second outer diameter, wherein the second outer diameter is greater than the first outer diameter and the sections having windings of the second outer diameter provide the interference contact with the energy dissipating structure.

3. The medical electrical lead of claim 2, wherein the lumen defined by the conductive material of the energy dissipating structure has an inner diameter and the second outer diameter of the sections of the coiled conductor is approximately equal to the inner diameter of the lumen defined by the conductive material of the energy dissipating structure.

4. The medical electrical lead of claim 2, wherein the lumen defined by the conductive material of the energy dissipating structure has an inner diameter and the second outer diameter of the sections of the coiled conductor is larger than the inner diameter of the lumen defined by the conductive material of the energy dissipating structure.

5. The medical electrical lead of claim 1, wherein the coiled conductor has a pre-formed geometry such that the portion of the coiled conductor extending through the lumen defined by the energy dissipating structure provides the interference contact with the energy dissipating structure.

6. The medical electrical lead of claim 5, wherein the portion of the coiled conductor extending through the lumen defined by the energy dissipating structure is shaped into one of an arc and an undulated pattern.

7. The medical electrical lead of claim 6, wherein the interference contact between the energy dissipating structure and the portion of the coiled conductor extending through the lumen defined by the energy dissipating structure is substantially continuous during movement of the lead.

8. The medical electrical lead of claim 5, the coiled conductor being pre-formed to include one of a J-shape or a loop toward a distal portion of the coiled conductor such that when the distal portion of the coiled conductor is placed within the lumen defined by the energy dissipating structure, spring-like properties of the coiled conductor wanting to return to its pre-formed shape results in the interference contact with the energy dissipating structure.

9. The medical electrical lead of claim 1, wherein a large portion of current induced on the coiled conductor by high frequency signals is redirected to the energy dissipating structure while a small portion of the current produced on the coiled conductor by low frequency therapy signals is redirected to the energy dissipating structure.

10. The medical electrical lead of claim 1, wherein the coupling of the conductive electrode shaft, the coiled conductor, and the electrode provides a mechanical relationship that allows for mechanical control of the electrode to extend the electrode from the distal end of the lead body.

11. The medical electrical lead of claim 1, wherein the coupling of the conductive electrode shaft, the coiled conductor, and the electrode provides a mechanical relationship that allows for mechanical control of the electrode to extend the electrode from the distal end of the lead body while the energy dissipating structure remains stationary.

12. An implantable medical system comprising:
an implantable medical device; and
an implantable medical electrical lead, wherein the implantable medical electrical lead includes:
a lead body having a proximal end configured to couple to the implantable medical device and a distal end;
a conductive electrode shaft located near the distal end within the lead body;
a coiled conductor extending within the lead body from the proximal end and coupled to a first end of the conductive electrode shaft;
an electrode located near the distal end of the lead body and coupled to an opposite end of the conductive electrode shaft as the coiled conductor;
an energy dissipating structure located near the distal end of the lead body and formed from a conductive material that defines a lumen through which a portion of the coiled conductor extends, wherein the portion of the coiled conductor extending through the lumen defined by the energy dissipating structure is configured to provide an interference contact with the energy dissipating structure that is substantially continuous; and
a layer of insulating material covering at least an outer surface of the conductive material of the energy dissipating structure such that the outer surface of the conductive material of the energy dissipating structure does not directly contact a body of the patient when implanted.

13. The medical electrical system of claim 12, wherein the portion of the coiled conductor extending through the lumen defined by the energy dissipating structure is formed to have one or more sections having windings of a first outer diameter and one or more sections having windings of a second outer diameter, wherein the second outer diameter is greater than the first outer diameter and is at least approximately equal to an inner diameter of the lumen defined by the conductive material of the energy dissipating structure such that the sections having windings of the second outer diameter provide the interference contact with the energy dissipating structure.

14. The medical electrical system of claim 12, wherein the coiled conductor has a pre-formed geometry such that the portion of the coiled conductor extending through the lumen defined by the energy dissipating structure provides the interference contact with the energy dissipating structure.

15. The medical electrical system of claim 14, wherein the portion of the coiled conductor extending through the lumen defined by the energy dissipating structure is shaped into one of an arc and an undulated pattern.

16. The medical electrical system of claim 15, the coiled conductor being pre-formed to include one of a J-shape or a loop toward a distal portion of the coiled conductor such that when the distal portion of the coiled conductor is placed within the lumen defined by the energy dissipating structure, spring-like properties of the coiled conductor wanting to return to its pre-formed shape results in the interference contact with the energy dissipating structure having one of the arc or the undulated pattern.

17. The medical electrical system of claim 12, wherein the coupling of the conductive electrode shaft, the coiled conductor, and the electrode provides a mechanical relationship that allows for mechanical control of the electrode to extend the electrode from the distal end of the lead body while the energy dissipating structure remains stationary.

18. A medical electrical lead comprising:
a lead body having a proximal end configured to couple to an implantable medical device and a distal end;
an electrode located near the distal end of the lead body;
a coiled conductor extending within the lead body from the proximal end and coupled to the electrode;
an energy dissipating structure located near the distal end of the lead body and formed from a conductive material that defines a lumen through which a portion of the coiled conductor extends, wherein the portion of the coiled conductor extending through the lumen defined by the energy dissipating structure is formed to provide an interference contact with the energy dissipating structure that is substantially continuous; and
a layer of insulating material covering at least an outer surface of the conductive material of the energy dissipating structure such that the outer surface of the conductive material of the energy dissipating structure does not directly contact a body of the patient when implanted.

19. The medical electrical lead of claim 18, wherein the portion of the coiled conductor extending through the lumen defined by the energy dissipating structure is formed to have one or more sections having windings of a first outer diameter and one or more sections having windings of a second outer diameter, wherein the second outer diameter is greater than the first outer diameter and is at least approximately equal to an inner diameter of the lumen defined by the conductive material of the energy dissipating structure such that the sections having windings of the second outer diameter provide the interference contact with the energy dissipating structure.

20. The medical electrical lead of claim 18, wherein the coiled conductor has a pre-formed geometry such that the portion of the coiled conductor extending through the lumen defined by the energy dissipating structure provides the interference contact with the energy dissipating structure.

21. The medical electrical lead of claim 20, wherein the portion of the coiled conductor extending through the lumen defined by the energy dissipating structure is shaped into one of an arc and an undulated pattern.

22. The medical electrical lead of claim 21, the coiled conductor being pre-formed to include one of a J-shape or a loop toward a distal portion of the coiled conductor such that when the distal portion of the coiled conductor is placed within the lumen defined by the energy dissipating structure, spring-like properties of the coiled conductor wanting to return to its pre-formed shape results in the interference contact with the energy dissipating structure having one of the arc or the undulated pattern.

* * * * *